(12) United States Patent
Wolff et al.

(10) Patent No.: US 8,822,473 B2
(45) Date of Patent: *Sep. 2, 2014

(54) METHOD OF TREATING DIABETES

(75) Inventors: Andrew Wolff, San Francisco, CA (US); Marcus Jerling, Bromma (SE)

(73) Assignee: Gilead Sciences, Inc., Foster City, CA (US)

(*) Notice: Subject to any disclaimer, the term of this patent is extended or adjusted under 35 U.S.C. 154(b) by 398 days.

This patent is subject to a terminal disclaimer.

(21) Appl. No.: 11/756,499

(22) Filed: May 31, 2007

(65) Prior Publication Data

US 2008/0009503 A1    Jan. 10, 2008

Related U.S. Application Data

(63) Continuation-in-part of application No. 10/443,314, filed on May 21, 2003.

(60) Provisional application No. 60/382,781, filed on May 21, 2002, provisional application No. 60/459,332, filed on Mar. 31, 2003.

(51) Int. Cl.
*A61K 31/495* (2006.01)
*A61P 3/10* (2006.01)
*A61P 3/06* (2006.01)

(52) U.S. Cl.
USPC .................................................. 514/252.12

(58) Field of Classification Search
None
See application file for complete search history.

(56) References Cited

U.S. PATENT DOCUMENTS

| | | | |
|---|---|---|---|
| 3,845,770 A | | 11/1974 | Theeuwes et al. |
| 4,173,626 A | * | 11/1979 | Dempski et al. .............. 424/462 |
| 4,326,525 A | | 4/1982 | Swanson et al. |
| 4,567,264 A | | 1/1986 | Kluge et al. |
| 4,902,514 A | | 2/1990 | Barclay et al. |
| 4,992,445 A | | 2/1991 | Lawter et al. |
| 5,001,139 A | | 3/1991 | Lawter et al. |
| 5,023,252 A | | 6/1991 | Hseih |
| 5,278,192 A | * | 1/1994 | Fung et al. ..................... 514/645 |
| 5,472,707 A | | 12/1995 | Samuels et al. |
| 5,506,229 A | | 4/1996 | Dow et al. |
| 5,616,345 A | | 4/1997 | Geoghegan et al. |
| 6,303,607 B1 | * | 10/2001 | Wolff et al. .............. 514/252.12 |
| 6,369,062 B1 | | 4/2002 | Wolff et al. |
| 6,423,705 B1 | | 7/2002 | Tracey et al. |
| 6,479,496 B1 | * | 11/2002 | Wolff ....................... 514/252.17 |
| 6,503,911 B2 | | 1/2003 | Wolff et al. |
| 6,525,057 B2 | * | 2/2003 | Wolff et al. ................ 514/252.1 |
| 6,528,511 B2 | * | 3/2003 | Wolff et al. .............. 514/252.12 |
| 6,562,826 B1 | * | 5/2003 | Wolff ....................... 514/252.12 |
| 6,617,328 B2 | | 9/2003 | Wolff et al. |
| 6,620,814 B2 | * | 9/2003 | Wolff et al. .............. 514/252.17 |
| 6,677,342 B2 | * | 1/2004 | Wolff et al. .............. 514/252.12 |
| 6,706,689 B2 | | 3/2004 | Coolidge et al. |
| 6,852,724 B2 | | 2/2005 | Wolff et al. |
| 6,864,258 B2 | * | 3/2005 | Wolff ....................... 514/252.12 |
| 6,930,111 B2 | | 8/2005 | Ibrahim et al. |
| 6,958,352 B2 | | 10/2005 | Pei et al. |
| 7,087,394 B2 | | 8/2006 | Johnson et al. |
| 2002/0042405 A1 | | 4/2002 | Schuh |
| 2002/0052377 A1 | * | 5/2002 | Wolff et al. .............. 514/252.12 |
| 2003/0055027 A1 | | 3/2003 | Schun |
| 2003/0069221 A1 | | 4/2003 | Kosoglou et al. |
| 2003/0181352 A1 | | 9/2003 | Ibrahim et al. |
| 2003/0220310 A1 | | 11/2003 | Schuh |
| 2003/0220312 A1 | | 11/2003 | Schuh |
| 2003/0220344 A1 | | 11/2003 | Belardinelli et al. |
| 2004/0063717 A1 | | 4/2004 | Wolff et al. |
| 2004/0097514 A1 | | 5/2004 | Wolff et al. |
| 2004/0198693 A1 | | 10/2004 | DeNinno et al. |
| 2005/0020682 A1 | | 1/2005 | Newell et al. |
| 2005/0054695 A1 | | 3/2005 | Ehring et al. |
| 2005/0059667 A1 | | 3/2005 | Wolff |
| 2005/0153982 A1 | | 7/2005 | Wolff |
| 2005/0245502 A1 | | 11/2005 | Keller |
| 2006/0100189 A1 | | 5/2006 | Gurtner et al. |
| 2006/0140953 A1 | | 6/2006 | Newell et al. |
| 2006/0147521 A1 | | 7/2006 | Wolff et al. |
| 2006/0172923 A1 | | 8/2006 | Seipke et al. |
| 2006/0177502 A1 | | 8/2006 | Sastry et al. |
| 2006/0205727 A1 | | 9/2006 | Kaesemeyer |

(Continued)

FOREIGN PATENT DOCUMENTS

| | | |
|---|---|---|
| EP | 1541175 | 6/2005 |
| FR | 2805463 | 8/2001 |

(Continued)

OTHER PUBLICATIONS

DeQuattro et al., "Comparative Antianginal Efficacy and tolerability of Ranolazine in Diabetic and Nondiabetic Patients: Results of the MARISA Trial," Abstracts—Myocardial Ischemia and Infarction, JACC, Feb. 2001, vol. 37, Issue 2, Supplement 1, p. 338A.*
Press Release of (Mar. 19, 2011) "CV Therapeutics Announces Phase III Marisa Analysis Suggesting Potential Benefit in Diabetic Patients With Chronic Angina," [retrieved on Apr. 30, 2012] Retrieved from the Internet: URL: www.evaluatepharma.com.*
Rohlfing et al: Defining the relationship between plasma glucose and HbA1c, Diabetes Care, vol. 25, No. 2, Feb. 2002, pp. 275-278.
Grundy et al: Prevention conference VI: diabetes and cardiovascular disease executive summary conference proceeding healthcare for professionals from a special writing group of the American Heart Association, Circulation, vol. 105, 2002; pp. 2231-2239.

(Continued)

*Primary Examiner* — Sreeni Padmanabhan
*Assistant Examiner* — Jody Karol
(74) *Attorney, Agent, or Firm* — Sheppard Mullin Richter & Hampton LLP

(57) ABSTRACT

Methods are provided for lowering plasma level of HbA1c in a diabetic, pre-diabetic, or non-diabetic patient suffering from at least one cardiovascular disease and slowing or delaying the development of or worsening of hyperglycemia in a diabetic, pre-diabetic, or non-diabetic patient.

10 Claims, 8 Drawing Sheets

(56) References Cited

U.S. PATENT DOCUMENTS

| | | |
|---|---|---|
| 2006/0217397 A1 | 9/2006 | Wolff et al. |
| 2008/0009503 A1 | 1/2008 | Wolff et al. |
| 2008/0153840 A1 | 6/2008 | Belardinelli et al. |
| 2008/0193530 A1 | 8/2008 | Blackburn et al. |
| 2008/0214555 A1 | 9/2008 | Jerling |
| 2008/0214556 A1 | 9/2008 | Jerling et al. |
| 2008/0233191 A1 | 9/2008 | Blackburn et al. |
| 2008/0248112 A1 | 10/2008 | Blackburn et al. |
| 2008/0299195 A1 | 12/2008 | Blackburn et al. |
| 2009/0111826 A1 | 4/2009 | Lange et al. |
| 2009/0203707 A1 | 8/2009 | Rajamani et al. |
| 2009/0312340 A1 | 12/2009 | Wang et al. |
| 2010/0035890 A1 | 2/2010 | Lange et al. |
| 2010/0197701 A1 | 8/2010 | Wolff et al. |

FOREIGN PATENT DOCUMENTS

| | | |
|---|---|---|
| WO | WO 00/13687 | 3/2000 |
| WO | WO 01/66093 | 9/2001 |
| WO | WO 02/07716 | 1/2002 |
| WO | WO 02/09761 | 2/2002 |
| WO | WO 03/008411 | 1/2003 |
| WO | WO 03/099281 | 12/2003 |
| WO | WO 2006/074398 | 7/2006 |
| WO | WO 2008/100992 | 8/2008 |
| WO | WO 2008/147417 | 12/2008 |
| WO | WO 2009/102886 | 8/2009 |

OTHER PUBLICATIONS

Redberg et al: Prevention conference VI: diabetes and cardiovascular disease, writing group III: risk assessment in persons with diabetes, Circulation, vol. 105, 2002; pp. e144-e152.

Hanck et al: Modification of inactivation in cardiac sodium channels: Ionic current studies with Anthopleurin-A toxin, J. Gen. Physiol., vol. 106, Oct. 1995, pp. 601-616.

Nuyens et al: Abrupt rate accelerations or premature beats cause life-threatening arrhythmias in mice with long-QT3 syndrome, Nature Medicine, vol. 7, No. 9, Sep. 2001, pp. 1021-1027.

El-Sherif et al: QTU prolongation and polymorphic ventricular tachyarrhythmias due to bradycardia-dependent early afterdepolarizations, Circulation Research, vol. 63, No. 2, Aug. 1988, pp. 286-305.

Splawski et al: Variant of SCN5A sodium channel implicated in risk of cardiac arrhythmia, Science Magazine, vol. 297, Aug. 23, 2003, pp. 1333-1336.

Chiang et al: The long QT syndromes: genetic basis and clinical implications, Journal of the American College of Cardiology, vol. 36, No. 1, 2000, pp. 1-12.

Viswanathan et al: Pause induced early afterdepolarizations in the long QT syndrome: a simulation study, Cardiovascular Research, vol. 42, 1999, pp. 530-542.

Glatter et al: Chemical cardioversion of atrial fibrillation or flutter with ibutilide in patients receiving amiodarone therapy, Circulation, vol. 103, 2001, pp. 253-257.

Diabetes Control and Complications Trial, National Institute of Diabetes and Digestive and Kidney Diseases (NIDDK), Results of the DCCT are reported in the New England Journal of Medicine, 329(14), Sep. 30, 1993.

Diabetes Prevention Program, National Institute of Diabetes and Digestive and Kidney Diseases (NIDDK), Results of the DCCT are reported in the New England Journal of Medicine, 329(14), Sep. 30, 1993.

Barnett et al; The Longitudinal Effect of Inhibiting Fatty Acid Oxidation in Diabetic Rats Fed a High Fat Diet, Database Biosis Online! Biosciences Information Service, Philadelphia PA, US, vol. 24, No. 8, 1992, pp. 360-362.

Randle, Apparent Reversal of Insulin Resistance in Cardiac Muscle in Alloxan Diabetes by 2 Bromo Stearate, Nature, London, vol. 221, No. 5182, 1969, p. 777, col. 1, line 66-69, col. 2, line 3-8;table 1.

Stanley et al, Regulation of Myocardial Carbohydrate Metabolism Under Normal and Ischaemic Condition Potential for Pharmacological Interventions, Cardiovascular Research, vol. 33, No. 2, Feb. 1997, pp. 243-257, p. 249, col. 2, line 8-17, p. 250, col. 1, line 13-19, p. 251, col. 1, paragraph 6,4, p. 252, paragraphs 6.6, 6.7.

Rohlfing et al: Defining the relationship between plasma glucose and HbA1c, Diabetes Care, vol. 25, No. 2, Feb. 2002, pp. 275-278.

Phillipov, Clinical Chemistry, 47(10), (2001), 1851-1853.

Barnett et al: The Longitudinal Effect of Inhibiting Fatty Acid Oxidation in Diabetic Rats Fed a High Fat Diet, Database Biosis Online! Biosciences Information Service, Philadelphia PA, US, vol. 24, No. 8, 1992, pp. 360-362.

Chase, et al., Annals of Emergency Medicine, 48(3):252-259 (2006).

Sadanandan, et al., J Am Coll Cardiol., 44(4):799-803 (2004).

Conway, et al., Heart, 92:1333-1334 (2006).

Lopaschuk, Abnormal Mechanical Function in Deabetes: Relationship to Altered Myocardial Carbohydrate/lipid Metabolism, Review in Depth, 7(2) 116-123, (1996).

Chaitman, B.R. et al, "Ranolazine Increases Exercise Performance and Decreases Hemoglobin A1C in Angina Patients with Diabetes", vol. 41, No. 6, Mar. 19, 2003, p. 378A.

Chaitman, B. et al., "189 Ranolazine Decreases Haemoglobin A1C (HbA1c) in Angina Patients with Diabetes: Carbohydrate and Lipid Parameters in MARISA and CARISA", European Heart Journal, the European Society of Cardiology, vol. 24, No. 5, Mar. 2003, p. 21.

Timmis, A.D. et al, "Effects of Ranolazine on Exercise Tolerance and HbA1c in Patients with Chronic Angina and Diabetes", European Heart Journal, vol. 27, Mar. 2006, pp. 42-48.

Cooper-Dehoff, R. & Pepine, C.J., "Ranolazine is Associated with Cardiovascular and Metabolic Improvements: a Win-Win for Patients with Diabetes", European Heart Journal, vol. 27, Mar. 2006, pp. 5-6.

Chen et al., SNP S1103Y in the Cardiac Sodium Channel Gene SCN5A is Associated with Cardiac Arrhythmias and Sudden Death in a White Family, J Med Genet, 2002; 39: 913-915.

Moss et al., Ranolazine Shortens Repolarization in Patients with Sustained Inward Sodium Current Due to Type-3 Long QT Syndrome, J Cardiovasc Electrophysiol, 2008; 19(12): 1289-1293.

Office Action for U.S. Appl. No. 12/556,417, dated Mar. 21, 2011.

Office Action for U.S. Appl. No. 12/755,931, dated Apr. 27, 2011.

Sabbah, et al., Partial fatty acid oxidation inhibitors—a potentially new class of drugs for heart failure, Euro J Heart Failure, 4:3-6 (2002).

Van Norstrand et al., Over Representation of the Pro-Arrhythmic, Sudden Death Predisposing Sodium Channel Polymorphism, S1103Y, in a Population Based Cohort of African American Sudden Infant Death Syndrome, Heart Rhythm, 2008; 5(5): 712-715.

Wedekind et al., De Novo Mutation in the SCN5A Gene Associated with Early Onset of Sudden Infant Death, Circulation, 2001; 104: 1158-1164.

U.S. Appl. No. 12/912,527, filed Oct. 20, 2010, Blackburn et al.

U.S. Appl. No. 12/972,949, filed Dec. 20, 2010, Belardinelli et al.

Abrams et al., "Ranolazine", Nat Rev Drug Discov., 5(6):453-5 (2006).

Chaitman et al., "Anti-ischemic effects and long-term survival during ranolazine monotherapy in patients with chronic severe angina" (2004) J Am Coll Cardiol, 43(8):1375-82 (2004).

Chaitman et al., "Effects of ranolazine with atenolol, amlodipine, or diltiazem on exercise tolerance and angina frequency in patients with severe chronic angina: a randomized controlled trial" JAMA, 291(3):309-16, (Nov. 2004).

Chaitman et al., "Efficacy of ranolazine as add-on therapy for chronic angina in elderly patients" Circulation, vol. 106 (19 Suppl. II): 330; Abstract No. 1649 (2002).

Chaitman et al., "Improved exercise capacity using a novel pFOX inhibitor as antianginal therapy: results of the combination assessment of ranolazine in stable angina (CARISA)", Circulation: Late Breaking Clinical Trial Abstracts, 104; pp. 1-2 (2001).

Chaitman et al., "Improved exercise performance on ranolazine in patients with chronic angina and a history of heart failure: The MARISA Trial", J Am Coll Cardiol, 37 (Suppl A):149A-150A; Abstract No. 1055-74 (2001).

(56) References Cited

OTHER PUBLICATIONS

Chaitman, "Measuring antianginal drug efficacy using exercise testing for chronic angina: improved exercise performance with ranolazine, a pFOX inhibitor", *Curr Probl Cardiol*, 27(12):527-55 (2002).

Chaitman, "Ranolazine for the treatment of chronic angina and potential use in other cardiovascular conditions", *Circulation*, 113:2462-2472 (2006).

Chaitman, "When should ranolazine be considered for the treatment of chronic angina?", *Nat Clin Pract Cardiovasc Med*, 3(11):590-1 (2006).

Morrow et al., "B-type natriuretic peptide and the effect of ranolazine in patients with non-ST-elevation acute coronary syndromes in the MERLIN-TIMI 36 trial", *Circulation, Supplemental II* 116(16):382: Abstract 1788 (2007).

Morrow et al., "Effect of ranolizine on hemoglobin a1c in the MERLIN-TIMI 36 randomized controlled trial", *Circulation* 116(16):Supplemental 539-540: Abstract 2453 (2007).

Morrow et al., "Effects of ranolazine on recurrent cardiovascular events in patients with non-ST-elevation acute coronary syndromes—The MERLIN-TIMI 36 Randomized Trial", *JAMA* 297(16):1775-1783; including Web-Only content (2007).

Morrow et al., "Evaluation of a novel anti-ischemic agent in acute coronary syndromes: design and rationale for the metabolic efficiency with ranolazine for less ischemia in non-ST-elevation acute coronary syndromes (MERLIN)-TIMI 36 trial", *Am Heart J* 151(6):1186.e1-1186.e9 (2006).

Morrow et al., "Evaluation of a novel anti-ischemic agent in acute coronary syndromes: design and rationale for the metabolic efficiency with ranolazine for less ischemia in non-ST-elevation acute coronary syndromes (MERLIN)-TIMI 36 trial", *Am Heart J* 152(2):400.e1-400.e9 (2006).

Office Action for U.S. Appl. No. 11/756,499, dated Apr. 1, 2010.
Office Action for U.S. Appl. No. 11/756,499, dated Oct. 3, 2011.
Office Action for U.S. Appl. No. 11/756,499, dated Sep. 22, 2009.
Office Action for U.S. Appl. No. 12/755,931, dated Sep. 12, 2011.
Office Action for U.S. Appl. No. 12/755,931, dated Feb. 28, 2012.

Press release of (Feb. 7, 2007) "MERLIN TIMI-36 study accepted as late breaking clinical trial at American College of Cardiology Annual Scientific Session" [retrieved on Feb. 7, 2007] Retrieved from the Internet: URL: http://prnewswire.com.

Press release of (Feb. 9, 2006) "CV Therapeutics announces MERLIN TIMI-36 study to continue as planned based on interim analysis" [retrieved on Feb. 7, 2007] Retrieved from the Internet: URL: http://prnewswire.com.

Press release of (Mar. 6, 2007) "CV Therapeutics Announces Topline MERLIN TIMI-36 Results" [retrieved on Oct. 3, 2008] Retrieved from the Internet: URL: http://prnewswire.com.

Press release of (May 25, 2006) "CV Therapeutics announces completion of MERLIN TIMI-36 enrollment" [retrieved on Feb. 7, 2007] Retrieved from the Internet: URL: http://prnewswire.com.

Press release of (Jun. 21, 2006) "MERLIN TIMI-36 study design published in American Heart Journal" [retrieved on Feb. 7, 2007] Retrieved from the Internet: URL: http://prnewswire.com.

Press release of (Jul. 7, 2006) "CV Therapeutics announces MERLIN TIMI-36 Study to continue as planned based on final scheduled DSMB meeting" [retrieved on Feb. 7, 2007] Retrieved from the Internet: URL: http://prnewswire.com.

Press release of (Jul. 29, 2004) "CV Therapeutics and FDA agree to special protocol assessment for outcomes study to support potential use of Ranexa™ as first-line therapy for chronic angina" [retrieved on Feb. 7, 2007] Retrieved from the Internet: URL: http://prnewswire.com.

Press release of (Sep. 26, 2007) "CV Therapeutics completes MERLIN TIMI-36 Study" [retrieved on Feb. 7, 2007] Retrieved from the Internet: URL: http://prnewswire.com.

Press release of (Oct. 11, 2004) "CV Therapeutics initiates MERLIN TIMI-36 Study of Ranexa™" [retrieved on Feb. 7, 2007] Retrieved from the Internet: URL: http://prnewswire.com.

Scirica et al., "Baseline clinical risk and recurrent ischemia as detected on continuous ECG (CECG) monitoring in patients with non-ST-elevation acute coronary syndrome in the MERLIN-TIMI 36 trial", *American Heart Association*, 116:II_722; Abstract No. 3211 (2007).

Scirica et al., "Clinical outcomes in patients with diabetes or the metabolic syndrome with non-ST-elevation acute coronary syndrome in the MERLIN-TIMI 36 trial", *Circulation*, pp. 64-65; Abstract No. P535 (2007).

Uusitupa et al., "Ten-year cardiovascular mortality in relation to risk factors and abnormalities in lipoprotein composition in type 2 [non-insulin-dependent] diabetic and non-diabetic subjects", *Diabetologia* vol. 36, pp. 1175-1184 (1993).

Wolff et al., "MARISA: Monotherapy assessment of ranolazine in stable angina", *JACC*, p. 408A Abstract No. 1196-101 (2000).

* cited by examiner

METHOD OF TREATING DIABETES

This is a Continuation-in-part of U.S. Non-Provisional patent application Ser. No. 10/443,314, filed on May 21, 2003, which claims priority to U.S. Provisional Application Ser. No. 60/382,781, filed May 21, 2002, and to U.S. Provisional Application Ser. No. 60/459,332, filed Mar. 31, 2003, the complete disclosures of which are hereby incorporated by reference.

FIELD OF THE INVENTION

Methods are provided for treating diabetes, lowering plasma level of HbA1c, in a diabetic, pre-diabetic, or non-diabetic patient suffering from at least one cardiovascular disease comprising administering ranolazine to these patients.

BACKGROUND

Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type TI, also known as insulin independent or non-insulin dependent diabetes (NIDDM). Both types of diabetes mellitus are due to insufficient amounts of circulating insulin and a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

Insulin lowers the concentration of glucose in the blood by stimulating the uptake and metabolism of glucose by muscle and adipose tissue. Insulin stimulates the storage of glucose in the liver as glycogen, and in adipose tissue as triglycerides. Insulin also promotes the utilization of glucose in muscle for energy. Thus, insufficient insulin levels in the blood, or decreased sensitivity to insulin, gives rise to excessively high levels of glucose and triglycerides in the blood.

The early symptoms of untreated diabetes mellitus are related to elevated blood sugar levels, and loss of glucose in the urine. High amounts of glucose in the urine can cause increased urine output and lead to dehydration. Dehydration causes increased thirst and water consumption. The inability to utilize glucose energy eventually leads to weight loss despite an increase in appetite. Some untreated diabetes patients also complain of fatigue, nausea, and vomiting. Patients with diabetes are prone to developing infections of the bladder, skin, and vaginal areas. Fluctuations in blood glucose levels can lead to blurred vision. Extremely elevated glucose levels can lead to lethargy and coma (diabetic coma).

People with glucose levels between normal and diabetic have impaired glucose tolerance (IGT). This condition is also called pre-diabetes or insulin resistance syndrome. People with IGT do not have diabetes, but rather have blood glucose levels that are higher than normal but not yet high enough to be diagnosed as diabetes. Their bodies make more and more insulin, but because the tissues don't respond to it, their bodies can't use sugar properly. Recent studies have shown that IGT itself may be a risk factor for the development of heart disease. It is estimated that people with pre-diabetes have a 1.5-fold risk of cardiovascular disease compared to people with normal blood glucose. People with diabetes have a 2- to 4-fold increased risk of cardiovascular disease.

High blood levels of glucose and triglycerides cause the thickening of capillary basement membrane, which results in the progressive narrowing of vessel lumina. The vasculopathies give rise to conditions such as diabetic retinopathy, which may result in blindness, coronary heart disease, intercapillary glomerulosclerois, neuropathy, and ulceration and gangrene of the extremities.

The toxic effects of excess plasma levels of glucose include the glycosylation of cells and tissues. Glycosylated products accumulate in tissues and may eventually form cross-linked proteins, which cross-linked proteins are termed advanced glycosylation end products. It is possible that non-enzymatic glycosylation is directly responsible for expansion of the vascular matrix and vascular complications of diabetes. For example, glycosylation of collagen results in excessive cross-linking, resulting in atherosclerotic vessels. Also, the uptake of glycosylated proteins by macrophages stimulates the secretion of pro-inflammatory cytokines by these cells. The cytokines activate or induce degradative and proliferative cascades in mesenchymal and endothelial cells respectively.

The glycosylation of hemoglobin provides a convenient method to determine an integrated index of the glycemic state. The level of glycosylated proteins reflects the level of glucose over a period of time and is the basis of an assay referred to as the hemoglobulin A1 (HbA1c) assay HbA1c reflects a weighted average of blood glucose levels during the previous 120 days; plasma glucose in the previous 30 days contributes about 50% to the final result in an HbA1c assay. The test for A1c (also known as HbA1c, glycohemoglobin, or glycated hemoglobin) indicates how well diabetes has been controlled over the last few months. The closer A1c is to 6%, the better the control of diabetes. For every 30 mg/dl increase in A1c blood glucose, there is a 1% increase in A1c, and the risk of complications increases.

Another explanation for the toxic effects of hyperglycemia includes sorbitol formation. Intracellular glucose is reduced to its corresponding sugar alcohol, sorbitol, by the enzyme aldose reductase; the rate of production of sorbitol is determined by the ambient glucose concentration. Thus, tissues such as lens, retina, arterial wall and schwann cells of peripheral nerves have high concentrations of sorbitol.

Hyperglycemia also impairs the function of neural tissues because glucose competes with myoinositol resulting in reduction of cellular concentrations and, consequently, altered nerve function and neuropathy.

Increased triglyceride levels are also a consequence of insulin deficiency. High triglyceride levels are also associated with vascular disease.

Thus, controlling blood glucose and triglyceride levels is a desirable therapeutic goal. A number of oral antihyperglycemic agents are known. Medications that increase the insulin output by the pancreas include sulfonylureas (including chlorpropamide [Orinase®], tolbutamide [Tolinase®], glyburide [Micronase®], glipizide [Glucotrol®], and glimepiride [Amaryl®]) and meglitinides (including reparglinide [Prandin®] and nateglinide [Starlix®]). Medications that decrease the amount of glucose produced by the liver include biguanides (including metformin [Glucophage®]. Medications that increase the sensitivity of cells to insulin include thazolidinediones (including troglitazone [Resulin®], pioglitazone [Actos®] and rosiglitazone [Avandia®]). Medications that decrease the absorption of carbohydrates from the intestine include alpha glucosidase inhibitors (including acarbose [Precose®] and miglitol [Glyset®]). Actos® and Avandia® can change the cholesterol patterns in diabetics. HDL (or good cholesterol) increases on these medications. Precose® works on the intestine; its effects are additive to diabetic medications that work at other sites, such as sulfonylureas. ACE inhibitors can be used to control high blood pressure, treat heart failure, and prevent kidney damage in people with hypertension or diabetes. ACE inhibitors or combination products of an ACE inhibitor and a diuretic, such as hydrochlorothazide, are marketed. However, none of these treatments is ideal.

Blood pressure control can reduce cardiovascular disease (for example, myocardial infarction and stroke) by approximately 33% to 50% and can reduce microvascular disease (eye, kidney, and nerve disease) by approximately 33%. The Center for Disease Control has found that for every 10 millimeters of mercury (mm Hg) reduction in systolic blood pressure, the risk for any complication related to diabetes is reduced by 12%. Improved control of cholesterol and lipids (for example HDL, LDL, and triglycerides) can reduce cardiovascular complications by 20% to 50%.

Total cholesterol should be less than 200 mg/dl. Target levels for high density lipoprotein (HDL or "good" cholesterol) are above 45 mg/dl for men and above 55 mg/dl for women, while low density lipoprotein (LDL or "bad" cholesterol) should be kept below 100 mg/dl. Target triglyceride levels for women and men are less than 150 mg/dl.

Approximately 50% of patients with diabetes develop some degree of diabetic retinopathy after 10 years of diabetes, and 80% of diabetics have retinopathy after 15 years.

In a study (the DCCT study) conducted by the National Institute of Diabetes and Digestive and Kidney Diseases (NIDDK) it was shown that keeping blood glucose levels as close to normal as possible slows the onset and progression of eye, kidney, and nerve diseases caused by diabetes.

In the Diabetes Prevention Program (DPP) clinical trial type 2 diabetics were studied. The DPP study found that over the 3 years of the study, diet and exercise sharply reduced the chances that a person with IGT would develop diabetes. Administration of metformin (Glucophage®) also reduced risk, although less dramatically.

The DCCT study showed a correlation between HbA1c and the mean blood glucose. The DPP study showed that HbA1c is strongly correlated with adverse outcome risk.

In a series of reports from the American Heart Association's Prevention Conference VI: Diabetes and Cardiovascular Disease it was reported that about two-thirds of people with diabetes eventually die of heart or blood vessel disease. Studies also showed that the increase in cardiovascular disease risk associated with diabetes can be lessened by controlling individual risk factors such as glucose level, obesity, high cholesterol, and high blood pressure.

It is important for a person suffering from diabetes to reduce the risk of complications such as cardiovascular disease, retinopathy, nephropathy, and neuropathy. It is also important for diabetics to reduce total cholesterol and triglyceride levels to reduce cardiovascular complications. Reduction of these possible complication risks is also important for a person suffering from IGT (a pre-diabetic).

Thus, if HbA1c and blood glucose levels can be controlled, the risk of complications such as cardiovascular disease, retinopathy, nephropathy, and neuropathy can be reduced or their onset delayed. If total cholesterol and triglyceride levels can be reduced, then cardiovascular complications can be reduced.

U.S. Pat. No. 4,567,264, the specification of which is incorporated herein by reference in its entirety, discloses ranolazine, (±)—N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction. In its dihydrochloride salt form, ranolazine is represented by the formula:

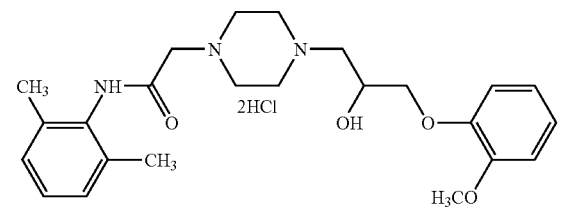 [SMILES: COc1ccccc1OCC(O)CN1CCN(CC(=O)Nc2c(C)cccc2C)CC1 ; "2HCl"]

This patent also discloses intravenous (IV) formulations of dihydrochloride ranolazine further comprising propylene glycol, polyethylene glycol 400, Tween 80 and 0.9% saline.

U.S. Pat. No. 5,506,229, which is incorporated herein by reference in its entirety, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. Oral and parenteral formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers. This patent also discloses IV ranolazine formulations which at the low end comprise 5 mg ranolazine per milliliter of an IV solution containing about 5% by weight dextrose. And at the high end, there is disclosed an IV solution containing 200 mg ranolazine per milliliter of an IV solution containing about 4% by weight dextrose.

The presently preferred route of administration for ranolazine and its pharmaceutically acceptable salts and esters is oral. A typical oral dosage form is a compressed tablet, a hard gelatin capsule filled with a powder mix or granulate, or a soft gelatin capsule (softgel) filled with a solution or suspension. U.S. Pat. No. 5,472,707, the specification of which is incorporated herein by reference in its entirety, discloses a high-dose oral formulation employing supercooled liquid ranolazine as a fill solution for a hard gelatin capsule or softgel.

U.S. Pat. No. 6,503,911, the specification of which is incorporated herein by reference in its entirety, discloses sustained release formulations that overcome the problem of affording a satisfactory plasma level of ranolazine while the formulation travels through both an acidic environment in the stomach and a more basic environment through the intestine, and has proven to be very effective in providing the plasma levels that are necessary for the treatment of angina and other cardiovascular diseases.

U.S. Pat. No. 6,852,724, the specification of which is incorporated herein by reference in its entirety, discloses methods of treating cardiovascular diseases, including arrhythmias variant and exercise-induced angina and myocardial infarction.

U.S. Patent Application Publication Number 2006/0177502, the specification of which is incorporated herein by reference in its entirety, discloses oral sustained release dosage forms in which the ranolazine is present in 35-50%, preferably 40-45% ranolazine. In one embodiment the ranolazine sustained release formulations of the invention include a pH dependent binder; a pH independent binder; and one or more pharmaceutically acceptable excipients. Suitable pH dependent binders include, but are not limited to, a methacrylic acid copolymer, for example Eudragit® (Eudragit® L100-55, pseudolatex of Eudragit® L100-55, and the like) partially neutralized with a strong base, for example, sodium hydroxide, potassium hydroxide, or ammonium hydroxide, in a quantity sufficient to neutralize the methacrylic acid copolymer to an extent of about 1-20%, for example about 3-6%. Suitable pH independent binders include, but are not limited to, hydroxypropylmethylcellulose (HPMC), for example Methocel® E10M Premium CR grade HPMC or Methocel® E4M Premium HPMC. Suitable pharmaceutically acceptable excipients include magnesium stearate and microcrystalline cellulose (Avicel® pH101).

In acute or emergency situations in which a patient either is or recently has experienced an acute cardiovascular disease event there is a need to initially and rapidly stabilize the patient. Once the patient has been stabilized there is a need to maintain the patient's stability by providing treatment over an extended period of time.

In diabetic, pre-diabetic, or non-diabetic coronary patients suffering from cardiovascular diseases there is a need to reduce the HbA1c level while treating the cardiovascular disease.

There is a need for a method for treating diabetic, pre-diabetic, or non-diabetic coronary patients suffering from an acute cardiovascular diseases comprising administering ranolazine in an intravenous (IV) formulation that provides therapeutically effective plasma concentrations of ranolazine in humans to treat the acute cardiovascular disease while reducing the HbA1c level of the patient.

There is also a need for a method for treating diabetic, pre-diabetic, or non-diabetic coronary patients suffering from cardiovascular diseases comprising administering ranolazine in an oral formulation that provides therapeutically effective plasma concentrations of ranolazine in humans to treat the cardiovascular disease while reducing the HbA1c level of the patient.

During angina clinical trials using ranolazine, it was surprisingly discovered that treatment of diabetic angina patients with ranolazine was not only effective in treating angina, but also reduced hemoglobulin A1 (HbA1c) levels and, over the long term, reduced triglyceride levels. Ranolazine was also found to reduce triglyceride levels in non-diabetic patients. Ranolazine was also found to lower glucose plasma levels and, over the long term, total cholesterol levels, while increasing HDL cholesterol levels. Thus, ranolazine provides a method of treating diabetes pre-diabetes, or the non-diabetes condition by reducing the levels of potentially toxic metabolites in blood and/or complications associated with diabetes. Ranolazine also can reduce the number of medications necessary for a patient with both cardiovascular problems and diabetes or pre-diabetes.

SUMMARY OF THE INVENTION

It is an object of this invention to provide an effective method of lowering the plasma level of HbA1c in a diabetic, pre-diabetic, or non-diabetic patient suffering from at least one cardiovascular disease while minimizing undesirable side effects.

Accordingly, in a first aspect, the invention relates to a method of lowering the plasma level of HbA1c in a diabetic, pre-diabetic, or non-diabetic patient suffering from at least one cardiovascular disease, comprising administration of a therapeutically effective amount of a compound of Formula I:

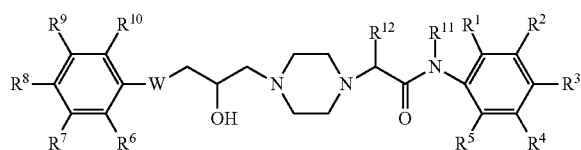

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkylamino; or $R^6$ and $R^7$ together form —CH=CH—CH=CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof, or an isomer thereof.

The compounds of Formula I are disclosed in more detail in U.S. Pat. No. 4,567,264, the complete disclosure of which is hereby incorporated by reference. A preferred compound of this invention is ranolazine, which is named N-(2,6-dimethylphenyl)-4-[2-hydroxy-3-(2-methoxyphenoxy)propyl]-1-piperazineacetamide, as a racemic mixture, or an isomer thereof, or a pharmaceutically acceptable salt thereof.

A second aspect of this invention is a method of lowering the plasma level of HbA1c in a diabetic, pre-diabetic, or non-diabetic patient suffering from at least one cardiovascular disease, wherein the cardiovascular disease is angina.

A third aspect of this invention is a method of lowering the plasma level of HbA1c in a diabetic, pre-diabetic, or non-diabetic patient suffering from at least one cardiovascular disease, wherein the cardiovascular disease is chronic angina.

A fourth aspect of this invention is a method of lowering the plasma level of HbA1c in a diabetic, pre-diabetic, or non-diabetic patient suffering from at least one cardiovascular disease, comprising administering a therapeutically effective amount of ranolazine.

A fifth aspect of this invention is a method of lowering the plasma level of HbA1c in a diabetic, pre-diabetic, or nondiabetic patient suffering from at least one cardiovascular disease, comprising administration of a therapeutically effective amount of a compound of Formula I:

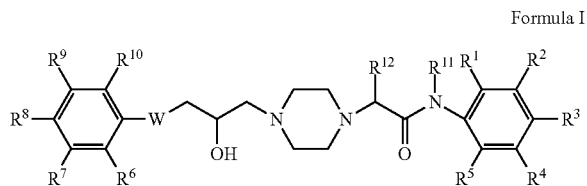

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkylamino; or $R^6$ and $R^7$ together form —CH═CH—CH═CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof, or an isomer thereof;

to a mammal in need thereof, wherein the compound of Formula I is administered as an immediate release formulation.

A sixth aspect of this invention is a method of lowering the plasma level of HbA1c in a diabetic, pre-diabetic, or non-diabetic patient suffering from at least one cardiovascular disease, comprising administration of a therapeutically effective amount of a compound of Formula I:

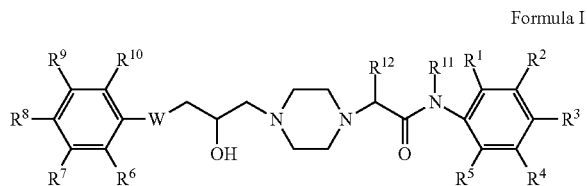

Formula I wherein:

$R^1$, $R^2$, $R^3$, $R^4$ and $R^5$ are each independently hydrogen, lower alkyl, lower alkoxy, cyano, trifluoromethyl, halo, lower alkylthio, lower alkyl sulfinyl, lower alkyl sulfonyl, or N-optionally substituted alkylamido, provided that when $R^1$ is methyl, $R^4$ is not methyl;

or $R^2$ and $R^3$ together form —OCH$_2$O—;

$R^6$, $R^7$, $R^8$, $R^9$ and $R^{10}$ are each independently hydrogen, lower acyl, aminocarbonylmethyl, cyano, lower alkyl, lower alkoxy, trifluoromethyl, halo, lower alkylthio, lower alkyl sulfinyl, lower alkyl sulfonyl, or di-lower alkylamino; or $R^6$ and $R^7$ together form —CH═CH—CH═CH—; or $R^7$ and $R^8$ together form —O—CH$_2$O—;

$R^{11}$ and $R^{12}$ are each independently hydrogen or lower alkyl; and

W is oxygen or sulfur;

or a pharmaceutically acceptable salt or ester thereof, or an isomer thereof;

to a mammal in need thereof, wherein the compound of Formula I is administered as a sustained release formulation.

A seventh aspect of this invention is a method of lowering the plasma level of HbA1c in a diabetic, pre-diabetic, or non-diabetic patient suffering from at least one cardiovascular disease, comprising administration of a therapeutically effective amount of a compound of Formula I to a mammal in need thereof, wherein the compound of Formula I is administered in a formulation that has both immediate release and sustained release aspects.

An eighth aspect of this invention is a method of lowering the plasma level of HbA1c in a diabetic, pre-diabetic, or non-diabetic patient suffering from at least one cardiovascular disease, comprising administration of a therapeutically effective amount of a sustained release formulation comprising a compound of Formula I to a mammal in need thereof, wherein the sustained release formulation provides a plasma level of ranolazine between 550 and 7500 ng base/ml over a 24 hour period.

A ninth aspect of the invention is a method of lowering the plasma level of HbA1c in a diabetic, pre-diabetic, or non-diabetic patient suffering from at least one cardiovascular disease, comprising administering a compound of Formula I wherein the dosage is from about 250 mg bid to about 2000 mg bid to a mammal.

A tenth aspect of this invention is a method of lowering the plasma level of HbA1c in a diabetic, pre-diabetic, or non-diabetic patient suffering from at least one cardiovascular disease, comprising administering from about 250 mg bid to about 2000 mg bid of ranolazine.

An eleventh aspect of this invention is a method of reducing negative consequences of diabetes comprising administration of ranolazine.

A twelfth aspect of this invention is a method of delaying or slowing the development of diabetes comprising administration of ranolazine.

A thirteenth aspect of this invention is a method of delaying the initiation of insulin treatment comprising administration of ranolazine.

A fourteenth aspect of this invention is a method of reducing HbA1c levels in a patient without leading to hypoglycemia comprising administration of ranolazine.

A fifteenth aspect of this invention is a method of delaying or slowing the development of worsening hyperglycemia in a diabetic, pre-diabetic, or non-diabetic patient suffering from at least one cardiovascular disease, comprising administration of ranolazine.

A sixteenth aspect of this invention is a method of reducing or slowing the development of hyperglycemia in a diabetic, pre-diabetic, or non-diabetic patient suffering from at least one cardiovascular disease, comprising administration of ranolazine.

BRIEF DESCRIPTION OF THE FIGURES

FIG. 8: Change in HbA1c (%). FIG. 8A shows

|          | M4        | M8        | M16       |
|----------|-----------|-----------|-----------|
| Placebo  | N = 770   | N = 598   | N = 122   |
| Ranolazine | N = 707 | N = 535   | N = 112   |
| P-value  | <0.001    | <0.001    | =0.13     |

Figures 8A, 8B:
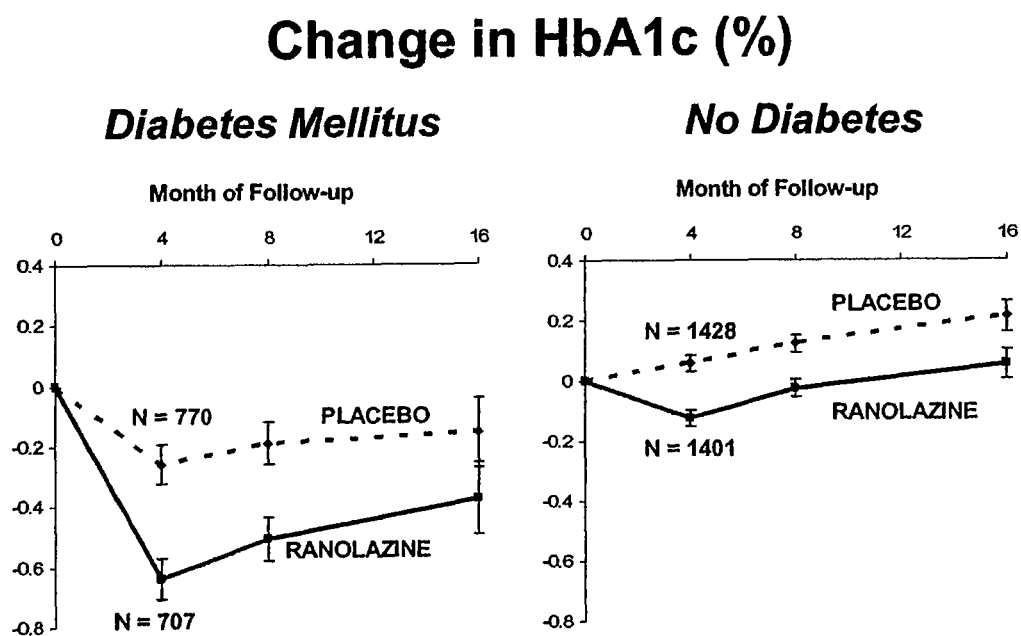
FIG. 8A shows the percentage change in HbA1a in patients diagnosed with diabetes mellitus before or at the start of randomization for this trial versus the months (16) of follow-up.

FIG. 8B shows the percentage change in HbA1c in patients that were either pre-diabetic or non-diabetic at the start of randomization for this trial (had not been diagnosed as diabetic before the start of this trial) versus the months (16) of follow-up. FIG. 8B shows

|          | M4        | M8        | M16       |
|----------|-----------|-----------|-----------|
| Placebo  | N = 1428  | N = 1113  | N = 260   |
| Ranolazine | N = 1401 | N = 1113 | N = 266   |
| P-value  | <0.001    | =0.002    | =0.025    |

DETAILED DESCRIPTION OF THE INVENTION

The invention provides a method of lowering the plasma level of HbA1c in a diabetic, pre-diabetic, or non-diabetic patient suffering from at least one cardiovascular disease, comprising administration of a compound of Formula I.

Diabetes, as defined herein, is a disease state characterized by hyperglycemia; altered metabolism of lipids, carbohydrates, and proteins; and an increased risk of complications from vascular disease.

Pre-diabetes, as defined herein, includes people with glucose levels between normal and diabetic have impaired glucose tolerance (IGT). This condition is also called pre-diabetes or insulin resistance syndrome. People with IGT do not have diabetes, but rather have blood glucose levels that are higher than normal but not yet high enough to be diagnosed as diabetes. Their bodies make more and more insulin, but because the tissues don't respond to it, their bodies can't use sugar properly.

Glycemic control is the regulation of blood glucose levels

Hemoglobin undergoes glycosylation on its amino terminal valine residue to form the glucosyl valine adduct of hemoglobin (HbA1c). The toxic effects of hyperglycemia may be the result of accumulation of such nonenzymatically glycosylated products. The covalent reaction of glucose with hemoglobin also provides a convenient method to determine an integrated index of the glycemic state. For example, the half-life of the modified hemoglobin is equal to that of the erythrocyte (about 120 days). Since the amount of glycosylated protein is proportional to the glucose concentration and the time of exposure of the protein to glucose, the concentration of HbA1c in the circulation reflects the glycemic state over an extended period (4 to 12 weeks) prior to sampling. Thus, a rise in HbA1c from 5% to 10% suggests a prolonged doubling of the mean blood glucose concentration With respect to the compound of Formula I, the following words and phrases are generally intended to have the meanings as set forth below, except to the extent that the context in which they are used indicates otherwise.

"Aminocarbonylmethyl" refers to a group having the following structure:

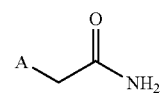

where A represents the point of attachment.

"Halo" or "halogen" refers to fluoro, chloro, bromo or iodo.

"Lower acyl" refers to a group having the following structure:

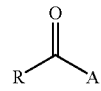

where R. is lower alkyl as is defined herein, and A represents the point of attachment, and includes such groups as acetyl, propanoyl, n-butanoyl and the like.

"Lower alkyl" refers to an unbranched saturated hydrocarbon chain of 1-4 carbons, such as methyl, ethyl, n-propyl, and n-butyl.

"Lower alkoxy" refers to a group —OR wherein R is lower alkyl as herein defined.

"Lower alkylthio" refers to a group —SR wherein R is lower alkyl as herein defined.

"Lower alkyl sulfinyl" refers to a group of the formula:

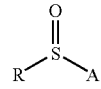

wherein R is lower alkyl as herein defined, and A represents the point of attachment.

"Lower alkyl sulfonyl" refers to a group of the formula:

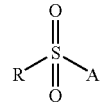

wherein R is lower alkyl as herein defined, and A represents the point of attachment.

"N-Optionally substituted alkylamido" refers to a group having the following structure:

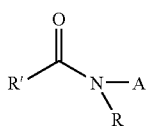

wherein R is independently hydrogen or lower alkyl and R' is lower alkyl as defined herein, and A represents the point of attachment.

The term "compound of Formula I" is intended to encompass the compounds of the invention as disclosed, and the pharmaceutically acceptable salts, pharmaceutically acceptable esters, and prodrugs of such compounds.

"Isomers" refers to compounds having the same atomic mass and atomic number but differing in one or more physical or chemical properties. All isomers of the compounds of Formula I, including the R- and S-enantiomers are within the scope of the invention.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The "patient" is a mammal, preferably a human.

Physiologically acceptable pH" refers to the pH of an intravenous solution which is compatible for delivery into a human patient. Preferably, physiologically acceptable pH's range from about 4 to about 8.5 and preferably from about 4 to 7. Without being limited by any theory, the use of intravenous solutions having a pH of about 4 to 6 are deemed physiologically acceptable as the large volume of blood in the body effectively buffers these intravenous solutions.

"Coronary diseases" or "cardiovascular diseases" refer to diseases of the cardiovasculature arising from any one or more than one of, for example, heart failure, including congestive heart failure, acute heart failure, ischemia, recurrent ischemia, myocardial infarction, arrhythmias, angina (including exercise-induced angina, variant angina, stable angina, unstable angina), acute coronary syndrome, diabetes, and intermittent claudication. The treatment of such disease states is disclosed in various U.S. patents and patent applications, including U.S. Pat. Nos. 6,503,911 and 6,528,511, U.S. Patent Application Serial Nos. 2003/0220344 and 2004/0063717, the complete disclosures of which are hereby incorporated by reference.

"An acute coronary disease event" refers to any condition relating to one or more coronary diseases which has/have manifested itself/themselves or has deteriorated to the point where the patient seeks medical intervention typically but not necessarily in an emergency situation.

"Acute coronary syndrome" or "ACS" refers to a range of acute myocardial ischemic states. It encompasses unstable angina and non-ST-segment elevation myocardial infarction (UA/NSTEMI), and ST segment elevation myocardial infarction (STEMI). STEMI refers to a complete occlusion by thrombus. In a preferred embodiment, ACS refers to those patients with a non-ST elevation acute coronary syndrome (NSTEACS). NSTEACS refers to a partial occlusion by the thrombus. NSTEACS is further defined as chest discomfort or anginal equivalent occurring at rest, lasting ≥10 minutes, and consistent with myocardial ischemia, and the presence of ischemic symptoms (≥5 minutes) at rest within 48 hours of admittance which may include index episode, and having at least one of the following indicators of moderate—high risk:

Elevated cardiac troponin (above local MI limit) or CK-MB (>ULN)
    ST-depression (horizontal or down-sloping)≥0.1 mV
    Diabetes mellitus (requiring insulin or oral therapy)
    A Risk Score of ≥3 wherein one point is assigned for each of the following variables and a total score calculated as the arithmetic sum:
        Age≥65 years;
        Known CAD (prior MI, CABG, PCI or angiographic stenosis ≥50%);
        Three or more cardiac risk factors (DM, elevated cholesterol, hypertension, family history);
        More than one episode of ischemic discomfort at rest in the prior 24 hours;
        Chronic aspirin use in the 7 days preceding onset of symptoms;
        ST segment depression ≥0.05 mV; and
        Elevated cardiac troponin or CK-MB.

These risk indicators are also referred to as TIMI (thrombolysis in myocardial ischemia) risk factors and are further discussed in Chase, et al., Annals of Emergency Medicine, 48(3):252-259 (2006); Sadanandan, et al., J Am Coll Cardiol., 44(4):799-803 (2004); and Conway, et al., Heart, 92:1333-1334 (2006), each of which is incorporated by reference in its entirety herein.

"Unstable angina" or "UA" refers to a clinical syndrome between stable angina and acute myocardial infarction. This definition encompasses many patients presenting with varying histories and reflects the complex pathophysiological mechanisms operating at different times and with different outcomes. Three main presentations have been described—angina at rest, new onset angina, and increasing angina.

"ECG" refers to an electrocardiogram.

"Cardiovascular intervention" or "coronary intervention" refers to any invasive procedure to treat a coronary disease including, but not limited to, "percutaneous coronary intervention" or PCI. It is contemplated that PCI encompasses a number of procedures used to treat patients with diseases of the heart. Examples of PCI include, but are not limited to, PTCA (percutaneous transluminal coronary angioplasty), implantation of stents, pacemakers, and other coronary devices, CABG (coronary artery bypass graft surgery) and the like.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Emergency" refers to an acute situation in which the patient is initially seen by medical personnel. Emergency situations can include, but are not limited to, medical facilities such as hospitals or clinics, emergency rooms at medical facilities such as hospitals or clinics, and emergency situations which involve police and/or medical personnel such as firemen, ambulance attendants, or other medically trained persons.

"Stabilized" or "stable" refers to a condition in which a patient is not considered to be in immediate risk of morbidity.

"Immediate release" ("IR") refers to formulations or dosage units that rapidly dissolve in vitro and are intended to be completely dissolved and absorbed in the stomach or upper gastrointestinal tract. Conventionally, such formulations release at least 90% of the active ingredient within 30 minutes of administration.

"Sustained release" ("SR") refers to formulations or dosage units used herein that are slowly and continuously dissolved and absorbed in the stomach and gastrointestinal tract over a period of about six hours or more. Preferred sustained release formulations are those exhibiting plasma concentrations of ranolazine suitable for no more than twice daily administration with two or less tablets per dosing as described below.

"Intravenous (IV) infusion" or "intravenous administration" refers to solutions or dosage units used herein that are provided to the patient by intravenous route. Such IV infusions can be provided to the patient until for up to about 96 hours in order to stabilize the patient's cardiovascular condition. The method and timing for delivery of an IV infusion is within the skill of the attending medically trained person.

"Renal insufficiency" refers to when a patient's kidneys no longer have enough kidney function to maintain a normal state of health. Renal insufficiency includes both acute and chronic renal failure, including end-stage renal disease (ESRD).

Methods of this Invention

As noted previously, in one aspect, this invention provides for a method for treating a diabetic, pre-diabetic, or non-diabetic patient suffering from an acute cardiovascular disease event. In a further embodiment of this aspect, the diabetic, pre-diabetic, or non-diabetic patient suffering from acute cardiovascular disease event exhibits one or more conditions associated with non-ST elevation acute coronary syndrome.

Patients presenting themselves with an acute coronary disease event include, but are not limited to, those who are being treated for one or more of the following: angina including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

The methods of this aspect of the invention are preferably achieved by administering to the presenting patient an IV solution comprising a selected concentration of ranolazine. Heretofore, the art provided IV solutions comprising ranolazine which comprised low concentrations of ranolazine (see, e.g., Kluge et al., U.S. Pat. No. 4,567,264 where Example 11 of that patent describes using 1.4 mg of ranolazine per mL in an IV solution comprising significant amounts of both propylene glycol (20 g/100 mL) and polyethylene glycol (20 g/100 mL)). Propylene glycol is a viscous liquid as is polyethylene glycol (see, e.g., the Merck Index, $12^{th}$ Ed., 1996). The increased viscosity resulting from the use of such IV solutions makes the rapid delivery of ranolazine to the patient suffering from an acute cardiovascular disease event more cumbersome and requires that a significant amount of propylene glycol and polyethylene glycol be co-administered.

Alternatively, the art provided IV solutions comprising ranolazine which comprised either high or very high concentrations of ranolazine (either 5 mg/mL or 200 mg/mL) relative to that employed in the IV solutions used herein. See, e.g., Dow, et al., U.S. Pat. No. 5,506,229. In an acute cardiovascular disease event where the patient is suffering from or at risk of suffering from renal insufficiency, the use of such concentrations of ranolazine can result in higher ranolazine plasma levels. Accordingly, the use of such concentrations is contraindicated for treating patients presenting with an acute cardiovascular disease event as the attending physician has little if any time to assess the renal function of that patient prior to initiating treatment.

In the methods of this invention, the IV solution has a selected amount of ranolazine comprising from about 1.5 to 3 mg per milliliter of solution, preferably about 1.8 to 2.2 mg per milliliter and, even more preferably, about 2 mg per milliliter. In contrast to Kluge, et al., supra., the IV solution does not contain any propylene glycol or any polyethylene glycol. Rather the compositions of this invention comprise ranolazine, sterile water and dextrose monohydrate or sodium chloride. As such, the compositions of this invention are less viscous than those described by Kluge et al. allowing for more efficient rapid titration of the patient with the IV solution.

The IV solution of this invention is different from the injectable formulations since injectable formulations typically have excipients that may not be needed and may be contraindicated for IV formulations of this invention. For example, an injectable formulation can have an anti-spasmodic agent such as gluconic acid. As such, the IV solutions of this invention do not contain such anti-spasmodic agents and especially gluconic acid.

The IV solution of this invention is used to stabilize a diabetic, pre-diabetic, or non-diabetic patient suffering from an acute cardiovascular disease event. In particular, the presenting patient is immediately administered this IV solution of ranolazine for a period until the patient is stabilized. Such stabilization typically occurs within from about 12 to about 96 hours.

In a preferred embodiment, the patient suffering from an acute cardiovascular disease event is treated by:

initiating administration of an IV solution to said patient wherein said IV solution comprises a selected concentration of ranolazine of from about 1.5 to about 3 mg per milliliter, preferably about 1.8 to about 2.2 mg per milliliter and, even more preferably, about 2 mg per milliliter;

titrating the IV administration of the IV ranolazine solution to the patient comprising: i) a sufficient amount of the IV solution to provide for about 200 mg of ranolazine delivered to the patient over about a 1 hour period; ii) followed by either: a sufficient amount of the IV solution to provide for about 80 mg of ranolazine per hour; or if said patient is suffering from renal insufficiency, a sufficient amount of the IV solution to provide for about 40 mg of ranolazine per hour; and maintaining the titration of b) above until the patient stabilizes which typically occurs within from about 12 to about 96 hours.

In one embodiment, the infusion of the intravenous formulation of ranolazine is initiated such that a target peak ranolazine plasma concentration of about 2500 ng base/mL (wherein ng base/mL refers to ng of the free base of ranolazine/mL) is achieved.

The downward adjustment of ranolazine infusion for a patient experiencing adverse events deemed to be treatment related, is within the knowledge of the skilled in the art and, based on the concentration of ranolazine in the IV solution, easy to achieve. Adverse events in addition to those described above include, but are not limited to, profound and persistent QTc prolongation, not attributed to other reversible factors such as hypokalemia; dizziness; nausea/vomiting; diplopia; parasthesia; confusion; and orthostatic hypotension. In one embodiment, the dose of intravenous solution of ranolazine may be adjusted to a lower dose such as, but not limited to, about 60 mg/hr, about 40 mg/hr, or about 30 mg/hr. In another embodiment, the intravenous delivery of ranolazine may be temporarily discontinued for 1-3 hrs and then restarted at the same or lower dose for patients experiencing adverse events deemed to be treatment related.

In a preferred embodiment, once stabilized the diabetic, pre-diabetic, or non-diabetic patient is then administered an oral sustained release formulation of ranolazine. Specifically, this invention is particularly useful for treating a high risk coronary disease patient with a subsequent acute coronary disease event by treating a patient with ranolazine. A high risk coronary patient is one who previously had at least one acute coronary disease event. In a preferred embodiment, a high risk patient has a TIMI risk score of 3 or higher.

In one embodiment, the oral dose of ranolazine is administered about 1 hour prior to the termination of the intravenous infusion of ranolazine. In one aspect of this embodiment, at the time of transition from intravenous to oral dose, for the intravenous dose of ranolazine of about 80 mg/hr, the oral dose administered is 1000 mg once or twice daily (2×500 mg). In another aspect of this embodiment, at the time of transition from intravenous to oral dose, for the intravenous dose of ranolazine of about 60 mg/hr, the oral dose administered is 750 mg once or twice daily (2×375 mg). In still another aspect of this embodiment, at the time of transition from intravenous to oral dose, for the intravenous dose of ranolazine of about 40 mg/hr, the oral dose administered is 500 mg (1×500 mg). In still another aspect of this embodiment, at the time of transition from intravenous to oral dose, for the intravenous dose of ranolazine of about 30 mg/hr, the oral dose administered is 375 mg (1×375 mg).

The downward adjustment of the oral dose for a patient experiencing adverse events deemed to be treatment related, is also within the knowledge of the skilled in the art. For example, the oral dose of ranolazine can be adjusted for patients with newly developed severe renal insufficiency. Other adverse events include, but are not limited to, profound and persistent QTc prolongation, not attributed to other reversible factors such as hypokalemia; dizziness; nausea/vomiting; diplopia; parasthesia; confusion; and orthostatic hypotension. In one embodiment, the oral dose of ranolazine may be adjusted downward to 500 mg once or twice daily, if not already at this dose or lower. In one embodiment, the oral dose of ranolazine may be adjusted to the next lower dose such as, but not limited to, 750 mg once or twice daily, 500 mg once or twice daily, or 375 mg once or twice daily.

In one embodiment, a starting oral dose of 375 mg once or twice daily may be administered to a patient treated with moderate CYP3A inhibitors, such as, diltiazem >180 mg/day, fluconazole and the like, and P-gp inhibitors such as, verapamil, cyclosporine and the like. In one embodiment, the 1000 mg oral dose of ranolazine is administered such that a mean peak ranolazine plasma concentration of about 2500 ng base/mL±1000 ng base/mL is achieved.

In one embodiment, the invention relates to a method for reducing ischemia associated with cardiovascular intervention in a patient comprising intravenously administering an intravenous formulation of ranolazine at least about 4 hours and preferably about 6 hours prior to intervention. In a further aspect of this embodiment, the invention further comprises continuing to administer the ranolazine intravenously for at least about 4 hours and preferably about 6 hours after the intervention.

In a preferred embodiment, a patient receives intravenous ranolazine for at least about 4 hours or at least about 6 hours prior to the intervention and then receives intravenous ranolazine for at least about 4 hours or at least about 6 hours after intervention.

In these embodiments of the invention, the ranolazine intravenously administered is an intravenous formulation as described herein.

Without limiting the scope of the invention, the formulations of the invention can be used for treating various diseases, such as, cardiovascular diseases e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g., congestive heart failure, acute heart failure, cardiac hypertrophy, etc.), restenosis after PTCA, PTCI (percutaneous transluminal coronary intervention), and shock (e.g., hemorrhagic shock, endotoxin shock, etc.); renal diseases e.g., diabetes mellitus, diabetic nephropathy, ischemic acute renal insufficiency, etc.; organ disorders associated with ischemia or ischemic reperfusion e.g., heart muscle ischemic reperfusion associated disorders, acute renal insufficiency, or disorders induced by surgical treatment such as CABG (coronary artery bypass grafting) surgeries, vascular surgeries, organ transplantation, non-cardiac surgeries or PTCA; cerebrovascular diseases e.g., ischemic stroke, hemorrhagic stroke, etc.; cerebro ischemic disorders e.g., disorders associated with cerebral infarction, disorders caused after cerebral apoplexy such as sequelae, or cerebral edema; and ischemia induced in donor tissues used in transplants where donor tissues include but are not limited to, renal transplants, skin grafts, cardiac transplants, lung transplants, corneal transplants, and liver transplants. The formulations of this invention can also be used as an agent for myocardial protection during CABG surgeries, vascular surgeries, PTCA, PTCI, organ transplantation, or non-cardiac surgeries.

Preferably, the formulations of this invention can be used for myocardial protection before, during, or after CABG surgeries, vascular surgeries, PTCA, organ transplantation, or non-cardiac surgeries. Preferably, the formulations of this invention can be used for myocardial protection in patients presenting with ongoing cardiac (acute coronary syndromes, e.g., myocardial infarction or unstable angina) or cerebral ischemic events (e.g., stroke). Preferably, the formulations of this invention can be used for chronic myocardial protection in patients with diagnosed coronary heart disease (e.g., previous myocardial infarction or unstable angina) or patients who are at high risk for myocardial infarction (age greater than 65 and two or more risk factors for coronary heart disease).

Compositions of the Invention
Intravenous Formulation

In one aspect, the invention provides an intravenous (IV) solution comprising a selected concentration of ranolazine. Specifically, the IV solution preferably comprises about 1.5 to about 3.0 mg of ranolazine per milliliter of a pharmaceutically acceptable aqueous solution, more preferably about 1.8 to about 2.2 mg and even more preferably about 2 mg. In order to allow for the rapid intravenous flow of ranolazine into the patient, the IV solution preferably contains no viscous components including by way of example as propylene glycol or polyethylene glycol (e.g., polyethylene glycol 400). It is understood that minor amounts of viscous components that do not materially alter the viscosity may be included in the intravenous formulations of this invention. In a particularly preferred embodiment, the viscosity of the IV solution is preferably less than 10 cSt (centistokes) at 20° C., more preferably less than 5 cSt at 20° C. and even more preferably less than 2 cSt at 20° C.

In one embodiment, the IV solution comprises:
about 1.5 to about 3.0 mg of ranolazine per mL of IV solution; and
either about 4.8 to about 5.0 weight percent dextrose or about 0.8 to about 1.0 weight percent sodium chloride.

In one embodiment, the IV solution comprises:
about 1.8 to about 2.2 mg of ranolazine per mL of IV solution; and
either about 4.8 to about 5.0 weight percent dextrose or about 0.8 to about 1.0 weight percent sodium chloride.

In one embodiment, the IV solution of this invention comprises:
about 2 mg of ranolazine per mL of IV solution; and
either about 4.8 to about 5.0 weight percent dextrose or about 0.9 weight percent sodium chloride.

The IV solutions described herein can be prepared from a stock solution comprising a 20 mL container for single use delivery which container comprises a sterile aqueous solution of ranolazine at a concentration of about 25 mg/mL; either about 36 mg/mL dextrose monohydrate or about 0.9 weight percent sodium chloride; and having a pH of about 4. Surprisingly, employing such high concentrations of ranolazine and dextrose monohydrate or ranolazine and sodium chloride in the stock solutions provide for compositions which are stable and have adequate shelf-lives, preferably of greater than 6 months.

Exemplary methods for preparing the stock solutions are described in Examples 1 and 2.

In a typical setting, two 20 mL containers described herein are injected into an IV container containing 460 mL of sterile saline (0.9 weight percent (w %) sodium chloride) or an aqueous dextrose solution (water containing 5 weight percent dextrose monohydrate) to provide for an IV solution of about 2 mg/mL of ranolazine maintained at physiologically acceptable pH. Containers useful herein include, but are not limited to, vials, syringes, bottles, IV bags, and the like.

In another embodiment, the intravenous formulation as above, is diluted with a sterile diluent prior to use. In one embodiment, the sterile diluent is 5% dextrose or a 0.9 weight percent saline solution. In one embodiment, the intravenous formulation is further diluted into bags of sterile diluent.

Oral Formulation

In one embodiment, a formulation of ranolazine is an oral formulation. In one embodiment, an oral formulation of ranolazine is a tablet. In one embodiment, the tablet of ranolazine is up to 500 mg. In another embodiment, the tablet of ranolazine is up to 1000 mg. In a preferred embodiment, the ranolazine tablet is 375 mg, and/or 500 mg.

The oral formulation of ranolazine is thoroughly discussed in U.S. Pat. No. 6,303,607 and U.S. Publication No. 2003/0220344, which are both incorporated herein by reference in their entirety.

The oral sustained release ranolazine dosage formulations of this invention are administered one, twice, or three times in a 24 hour period in order to maintain a plasma ranolazine level above the threshold therapeutic level and below the maximally tolerated levels, which is preferably a plasma level of about 550 to 7500 ng base/mL in a patient.

In a preferred embodiment, the plasma level of ranolazine ranges about 1500-3500 ng base/mL.

In order to achieve the preferred plasma ranolazine level, it is preferred that the oral ranolazine dosage forms described herein are administered once or twice daily. If the dosage forms are administered twice daily, then it is preferred that the oral ranolazine dosage forms are administered at about twelve hour intervals.

In addition to formulating and administering oral sustained release dosage forms of this invention in a manner that controls the plasma ranolazine levels, it is also important to minimize the difference between peak and trough plasma ranolazine levels. The peak plasma ranolazine levels are typically achieved at from about 30 minutes to eight hours or more after initially ingesting the dosage form while trough plasma ranolazine levels are achieved at about the time of ingestion of the next scheduled dosage form. It is preferred that the sustained release dosage forms of this invention are administered in a manner that allows for a peak ranolazine level no more than 8 times greater than the trough ranolazine level, preferably no more than 4 times greater than the trough ranolazine level, preferably no more than 3 times greater than the trough ranolazine level, and most preferably no greater than 2 times trough ranolazine level.

The sustained release ranolazine formulations of this invention provide the therapeutic advantage of minimizing variations in ranolazine plasma concentration while permitting, at most, twice-daily administration. The formulation may be administered alone, or (at least initially) in combination with an immediate release formulation if rapid achievement of a therapeutically effective plasma concentration of ranolazine is desired or by soluble IV formulations and oral dosage forms.

Without limiting the scope of the invention, the formulations of the invention can be used for treating various diseases, such as, cardiovascular diseases e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g., congestive heart failure, acute heart failure, cardiac hypertrophy, etc.), restenosis after PTCA, PTCI (percutaneous transluminal coronary intervention), and shock (e.g., hemorrhagic shock, endotoxin shock, etc.); renal diseases e.g., diabetes mellitus, impaired glucose tolerance or pre-diabetes, diabetic nephropathy, ischemic acute renal insufficiency, etc.; organ disorders associated with ischemia or ischemic reperfusion e.g., heart muscle ischemic reperfusion associated disorders, acute renal insufficiency, or disorders induced by surgical treatment such as CABG (coronary artery bypass grafting) surgeries, vascular surgeries, organ transplantation, non-cardiac surgeries or PTCA; cerebrovascular diseases e.g., ischemic stroke, hemorrhagic stroke, etc.; cerebro ischemic disorders e.g., disorders associated with cerebral infarction, disorders caused after cerebral apoplexy such as sequelae, or cerebral edema; and ischemia induced in donor tissues used in transplants where donor tissues include but are not limited to, renal transplants, skin grafts, cardiac transplants, lung transplants, corneal transplants, and liver transplants. The formulations of this invention can also be used as an agent for myocardial protection during CABG surgeries, vascular surgeries, PTCA, PTCI, organ transplantation, or non-cardiac surgeries.

Preferably, the formulations of this invention can be used for myocardial protection before, during, or after CABG surgeries, vascular surgeries, PTCA, organ transplantation, or non-cardiac surgeries. Preferably, the formulations of this invention can be used for myocardial protection in patients presenting with ongoing cardiac (acute coronary syndromes, e.g., myocardial infarction or unstable angina) or cerebral ischemic events (e.g., stroke). Preferably, the formulations of this invention can be used for chronic myocardial protection in patients with diagnosed coronary heart disease (e.g., previous myocardial infarction or unstable angina) or patients who are at high risk for myocardial infarction (age greater than 65 and two or more risk factors for coronary heart disease).

Pharmaceutical Compositions and Administration

The compounds of the invention are usually administered in the form of pharmaceutical compositions. This invention therefore provides pharmaceutical compositions that contain, as the active ingredient, one or more of the compounds of the invention, or an isomer thereof, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of the invention may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

One preferred mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the invention in the required amount in the appropriate solvent with various other ingredients as enumerated above, as required, followed by filtration and sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via tablet, capsule or enteric-coated tablets, or the like. In making the pharmaceutical compositions that include at least one compound of either Formula I, the active ingredient is usually diluted by an excipient and/or enclosed within a carrier such that the formulation can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845, 770; 4,326,525; 4,902,514; 5,616,345; and WO 0013687. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. Preferably, for oral administration, each dosage unit contains from 10 mg to 2 g of a compound of Formula I, more preferably 10 to 1500 mg, more preferably from 10 to 1000 mg, more preferably from 10 to 700 mg, and for parenteral administration, preferably from 10 to 700 mg of a compound of Formula I, more preferably about 50 to 200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In one embodiment, the preferred compositions of the invention are formulated so as to provide quick, sustained or delayed release of the active ingredient after administration to the patient, especially sustained release formulations. The most preferred compound of the invention is ranolazine, which is named (±)—N-(2,6-dimethylphenyl)-4-[2-hydroxy-3-(2 methoxyphenoxy)propyl]-1-piperazine-acetamide, or its isomers, or its pharmaceutically effective salts. Unless otherwise stated, the ranolazine plasma concentrations used in the specification and examples refer to ranolazine free base.

The preferred sustained release formulations of this invention are preferably in the form of a compressed tablet comprising an intimate mixture of compound and a partially neutralized pH-dependent binder that controls the rate of dissolution in aqueous media across the range of pH in the stomach (typically approximately 2) and in the intestine (typically approximately about 5.5). An example of a sustained release formulation is disclosed in U.S. Pat. Nos. 6,303,607; 6,479,496; 6,369,062; and 6,525,057, the complete disclosures of which are hereby incorporated by reference.

To provide for a sustained release of compound, one or more pH-dependent binders are chosen to control the dissolution profile of the compound so that the formulation releases the drug slowly and continuously as the formulation passed through the stomach and gastrointestinal tract. The dissolution control capacity of the pH-dependent binder(s) is particularly important in a sustained release formulation because a sustained release formulation that contains sufficient compound for twice daily administration may cause untoward side effects if the compound is released too rapidly ("dose-dumping").

Accordingly, the pH-dependent binders suitable for use in this invention are those which inhibit rapid release of drug from a tablet during its residence in the stomach (where the pH is below about 4.5), and which promotes the release of a therapeutic amount of compound from the dosage form in the lower gastrointestinal tract (where the pH is generally greater than about 4.5). Many materials known in the pharmaceutical art as "enteric" binders and coating agents have the desired pH dissolution properties. These include phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof.

Preferred pH-dependent binder materials that can be used in conjunction with the compound to create a sustained release formulation are methacrylic acid copolymers. Methacrylic acid copolymers are copolymers of methacrylic acid with neutral acrylate or methacrylate esters such as ethyl acrylate or methyl methacrylate. A most preferred copolymer is methacrylic acid copolymer, Type C, USP (which is a copolymer of methacrylic acid and ethyl acrylate having between 46.0% and 50.6% methacrylic acid units). Such a copolymer is commercially available, from Röhm Pharma as Eudragit® L 100-55 (as a powder) or L30D-55 (as a 30% dispersion in water). Other pH-dependent binder materials which may be used alone or in combination in a sustained release formulation dosage form include hydroxypropyl cellulose phthalate, hydroxypropyl methylcellulose phthalate, cellulose acetate phthalate, polyvinylacetate phthalate, polyvinylpyrrolidone phthalate, and the like.

One or more pH-independent binders may be in used in sustained release formulations in oral dosage forms. It is to be noted that pH-dependent binders and viscosity enhancing agents such as hydroxypropyl methylcellulose, hydroxypropyl cellulose, methylcellulose, polyvinylpyrrolidone, neutral poly(meth)acrylate esters, and the like, may not themselves provide the required dissolution control provided by the identified pH-dependent binders. The pH-independent binders may be present in the formulation of this invention in an amount ranging from about 1 to about 10 wt %, and preferably in amount ranging from about 1 to about 3 wt % and most preferably about 2.0 wt %.

As shown in Table 1, the preferred compound of the invention, ranolazine, is relatively insoluble in aqueous solutions having a pH above about 6.5, while the solubility begins to increase dramatically below about pH 6.

TABLE 1

| Solution pH | Solubility (mg/mL) | USP Solubility Class |
|---|---|---|
| 4.81 | 161 | Freely Soluble |
| 4.89 | 73.8 | Soluble |
| 4.90 | 76.4 | Soluble |
| 5.04 | 49.4 | Soluble |
| 5.35 | 16.7 | Sparingly Soluble |
| 5.82 | 5.48 | Slightly soluble |
| 6.46 | 1.63 | Slightly soluble |
| 6.73 | 0.83 | Very slightly soluble |
| 7.08 | 0.39 | Very slightly soluble |
| 7.59 (unbuffered water) | 0.24 | Very slightly soluble |
| 7.79 | 0.17 | Very slightly soluble |
| 12.66 | 0.18 | Very slightly soluble |

Increasing the pH-dependent binder content in the formulation decreases the release rate of the sustained release form of the compound from the formulation at pH is below 4.5 typical of the pH found in the stomach. The enteric coating formed by the binder is less soluble and increases the relative release rate above pH 4.5, where the solubility of compound is lower. A proper selection of the pH-dependent binder allows for a quicker release rate of the compound from the formulation above pH 4.5, while greatly affecting the release rate at low pH. Partial neutralization of the binder facilitates the conversion of the binder into a latex like film which forms around the individual granules. Accordingly, the type and the quantity of the pH-dependent binder and amount of the partial neutralization composition are chosen to closely control the rate of dissolution of compound from the formulation.

The dosage forms of this invention should have a quantity of pH-dependent binders sufficient to produce a sustained release formulation from which the release rate of the compound is controlled such that at low pHs (below about 4.5) the rate of dissolution is significantly slowed. In the case of methacrylic acid copolymer, type C, USP (Eudragit® L 100-55), a suitable quantity of pH-dependent binder is between 5% and 15%. The pH dependent binder will typically have from about 1 to about 20% of the binder methacrylic acid carboxyl groups neutralized. However, it is preferred that the degree of neutralization ranges from about 3 to 6%. The sustained release formulation may also contain pharmaceutical excipients intimately admixed with the compound and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth)acrylate esters (e.g. the methyl methacrylate/ethyl acrylate copolymers sold under the trademark Eudragit® NE by Röhm Pharma, starch, gelatin, sugars carboxymethylcellulose, and the like. Other useful pharmaceutical excipients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids are also optionally present.

The sustained release formulations of this invention have an active compound content of above about 50% by weight to about 95% or more by weight, more preferably between about 70% to about 90% by weight and most preferably from about 70 to about 80% by weight; a pH-dependent binder content of between 5% and 40%, preferably between 5% and 25%, and more preferably between 5% and 15%; with the remainder of the dosage form comprising pH-independent binders, fillers, and other optional excipients.

One particularly preferred sustained release formulations of this invention is shown below in Table 2.

TABLE 2

| Ingredient | Weight Range (%) | Preferred Range (%) | Most Preferred |
|---|---|---|---|
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

It has been found that these methods produce sustained release formulations that provide lower peak plasma levels and yet effective plasma concentrations of compound for up to 12 hours and more after administration, when the compound is used as its free base, rather than as the more pharmaceutically common dihydrochloride salt or as another salt or ester. The use of free base affords at least one advantage: The proportion of compound in the tablet can be increased, since the molecular weight of the free base is only 85% that of the dihydrochloride. In this manner, delivery of an effective amount of compound is achieved while limiting the physical size of the dosage unit.

Utility and Testing

The method is effective in the treatment of diabetes.

Activity testing is conducted as described in the Examples below, and by methods apparent to one skilled in the art.

The Examples that follow serve to illustrate this invention. The Examples are intended to in no way limit the scope of this invention, but are provided to show how to make and use the compounds of this invention. In the Examples, all temperatures are in degrees Centigrade.

Examples 1-4 illustrate the preparation of representative pharmaceutical formulations containing a compound of Formula I.

EXAMPLE 1

20-mL Type 1 flint vial of Ranolazine Injection filled to deliver 20 mL (at 1, 5, or mg/mL ranolazine concentration).
Compositions:

| Ranolazine | 1.0, 5.0, 25.0 mg/mL |
| Dextrose monohydrate | 55.0, 52.0, 36.0 mg/mL |
| Hydrochloric acid | q.s. pH to 4.0 ± 0.2 |
| Sodium hydroxide | q.s. pH to 4.0 ± 0.2 |
| Water for Injection | q.s. |

Container/Closure System:

| Vial: | Type 1 Flint, 20-cc, 20-mm finish |
| Stopper: | Rubber, 20-mm, West 4432/50, gray butyl, teflon coated |
| Seal: | Aluminum, 20-mm, flip-top oversea |

Method of Manufacture

The intravenous formulation of ranolazine is manufactured via an aseptic fill process as follows. In a suitable vessel, the required amount of dextrose monohydrate was dissolved in Water for Injection (WFI) at about 78% of the final batch weight. With continuous stirring, the required amount of ranolazine was added to the dextrose solution. To facilitate the dissolution of ranolazine, the solution pH was adjusted to a target of 3.88-3.92 with an 0.1 N or 1.0 N HCl solution. Additionally, 1 N NaOH may have been utilized to further adjust the solution to the target pH of 3.88-3.92. After ranolazine was dissolved, the batch was adjusted to the final weight with WFI. Upon confirmation that in-process specifications had been met, the ranolazine-formulated bulk solution was sterilized by sterile filtration through two 0.2 μm sterile filters. Subsequently, the sterile ranolazine-formulated bulk solution was aseptically filled into sterile glass vials and aseptically stoppered with sterile stoppers. The stoppered vials were then sealed with clean flip-top aluminum overseals. The vials then went through a final inspection.

EXAMPLE 2

20-mL Type 1 flint vial of Ranolazine Injection are filled to deliver 20 mL (25 mg/mL concentration).
Composition:

| Ranolazine | 25.0 mg/mL |
| Dextrose monohydrate | 36.0 mg/mL |
| Hydrochloric acid | Adjust pH to 3.3-4.7 |
| Water for Injection | q.s. |

Container/Closure System:

| Vial: | Type 1 tubing, untreated, 20-mL, 20-mm finish |
| Stopper: | Rubber, 20-mm, West 4432/50, gray butyl |
| Seal: | Aluminum, 20-mm, blue flip-off overseal |

Method of Manufacture

Water for Injection (WFI) is charged in a suitable vessel at about 90% of the final batch weight. About 90-95% of the required amount of 5 N HCl is added into the compounding vessel. With continuous stirring, the required amount of ranolazine is slowly added, followed by the addition of dextrose monohydrate into the ranolazine solution. To solubilize ranolazine, the solution pH is adjusted with 5 N HCl solution to a target of 3.9-4.1. The batch is subsequently adjusted to the final weight with WFI. Upon confirmation that in-process specifications have been met, the ranolazine-formulated bulk solution is sterilized by filtration through two redundant 0.22 μm sterilizing filters. The sterile ranolazine-formulated bulk solution is then aseptically filled into 20 mL sterile/depyrogenated vials and aseptically stoppered with sterile/depyrogenated stoppers. The stoppered vials are sealed with clean flip-top aluminum overseals. The sealed vials are terminally sterilized by a validated terminal sterilization cycle at 121.1° C. for 30 minutes. After the terminal sterilization process, the vials go through an inspection. To protect the drug product from light, the vials are individually packaged into carton boxes.

EXAMPLE 3

Patients with Diabetes or the Metabolic Syndrome Presenting with Non-ST-Elevation Acute Coronary Syndrome (NSTEACS)

Background

Data obtained from a clinical trial of patients admitted with non-ST elevation acute coronary syndrome (NSTEACS) was evaluated to determine the prevalence and outcome of those patients also suffering with diabetes and/or metabolic syndrome. The patients were treated with ranolazine which has been associated with improved glycemic parameters. See U.S. patent application Ser. No. 10/443,314, published as US 2004/0063717, incorporated by reference herein in its entirety.

Methods

MERLIN-TIMI 36 randomized 6560 patients at presentation with NSTEACS were treated with either placebo or the anti-ischemic agent ranolazine, which has also been associated with improved glycemic parameters. Median clinical follow-up was 12 months. Metabolic syndrome was defined as having any 3 of the following: 1) waist circumference ≥102 cm (men) and ≥88 cm (women), 2) triglycerides (TG) ≥150 mg/dL or drug treatment for elevated TG, 3) High density lipoproteins (HDL) <40 mg/dL (men) and <50 mg/dL (women), or drug treatment for reduced HDL, 4) Systolic blood pressure (SBP) ≥130 mmHg or diastolic blood pressure (DBP) ≥85 mmHg or drug treatment for hypertension, and 5) fasting glucose >100 mg/dL.

Results

Figure 1:
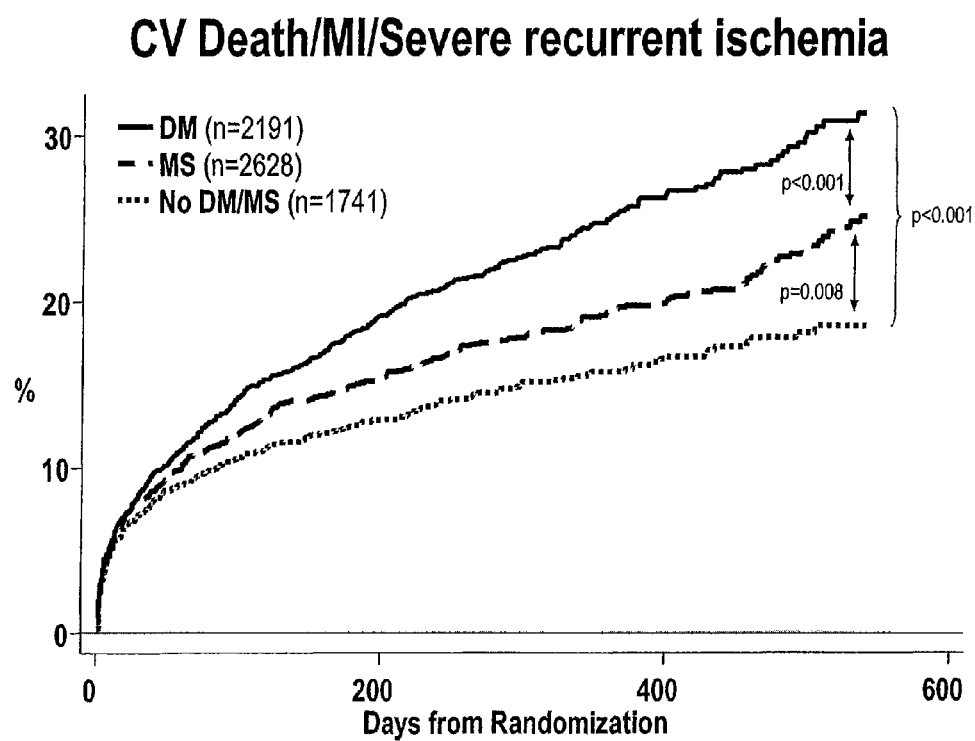
FIG. 1. CV Death/MI/Severe recurrent ischemia

At randomization, 2191 (33.4%) of all patient carried a diagnosis of diabetes mellitus (DM) and 2628 (40.1%) patients had metabolic syndrome. Patients with DM and metabolic syndrome were more likely to be female and have known coronary artery disease and had higher TIMI Risk scores at presentation, but were less likely to have an index diagnosis of NSTEMI (44.8% for DM v. 51.2% for metabolic syndrome v. 62.8% for no diagnosis, p<0.001). The rate of revascularization was similar among all groups (40.4% v. 39.7% v. 37.4%, p=0.11). There was a stepwise increase in the risk of severe recurrent ischemia, myocardial infarction, and cardiovascular death in patients with DM at highest risk followed by those with metabolic syndrome and then patients with neither at lowest risk. (FIG. 1).

Conclusions

Metabolic syndrome and diabetes are common among patients presenting with NSTEACS and confer increased cardiovascular risk.

EXAMPLE 4

Sustained release tablets containing the following ingredients are prepared:

| Ingredient | Weight Range (%) | A preferred Ranolazine Form'n (mg) |
|---|---|---|
| Ranolazine | 75 | 500 |
| Microcrystalline cellulose (filler) | 10.6 | 70.7 |
| Methacrylic acid copolymer | 10.0 | 66.7 |
| Sodium hydroxide | 0.4 | 2.7 |
| Hydroxypropyl methylcellulose | 2.0 | 13.3 |
| Magnesium stearate | 2.0 | 13.3 |

Compound and pH-dependent binder and any optional excipients are intimately mixed (dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg, and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 5

Hemoglobin A1c Assays

Figure 2:
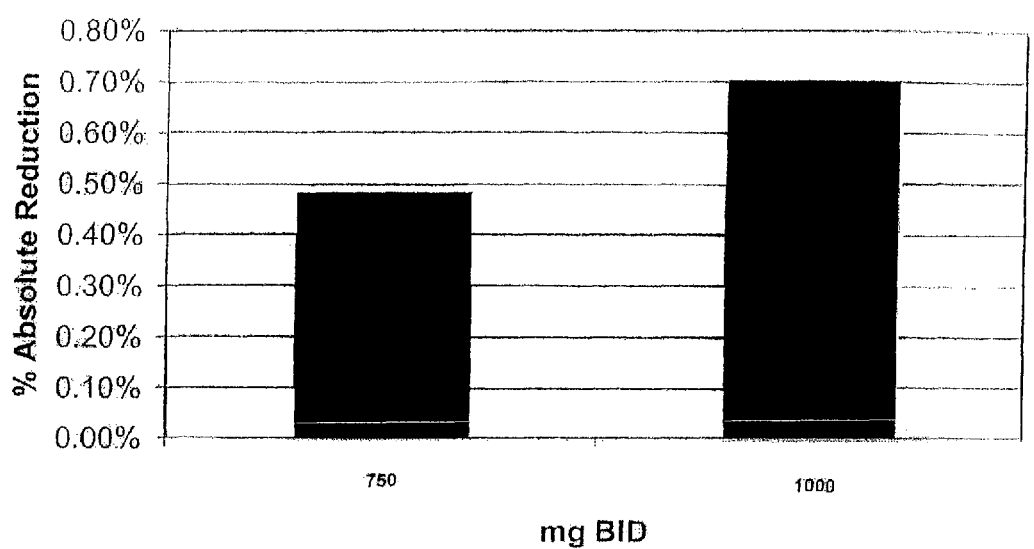
FIG. 2. Effect of Ranolazine on HbA1c Levels.

HbA1c levels were assayed following a modification of the method of Phillipov (Components of total measurement error for hemoglobin A1c determination. Phillipov, G., et al. Clin. Chem. (2001), 47(10):1851). (see FIG. 2)

EXAMPLE 6

Triglyceride Levels

Test compounds, dissolved in DMSO and suspended in 0.5% tylose, are administered perorally by means of a pharyngeal tube to Syrian gold hamsters. To determine the CETP activity, blood samples (approximately 250.mu.l) are taken by retro-orbital puncture prior to the start of the experiment. The compounds are subsequently administered perorally using a pharyngeal tube. Identical volumes of solvent without compounds are administered to the control animals. Subsequently, the animals are fasted. Then at various times, up to 24 hours after administration of the compounds, blood samples are taken by puncture of the retro-orbital venous plexus.

The blood samples are coagulated by incubation at 4° C. overnight. The samples are centrifuged at 6000×.g for 10 minutes. The concentration of cholesterol and triglycerides in the resulting serum are determined using modifications of commercially available enzyme tests (cholesterol enzymatic 14366 Merck, triglycerides 14364 Merck).

EXAMPLE 7

In order to study the anti-diabetic actions of the compounds, insulin-dependent diabetes mellitus can be induced by chemical destruction of the pancreas with an i.v. injection of STZ (60 mg/kg, controls can be given saline vehicle). The volume of the injection is equivalent to 0.1 ml/100 g body weight. The injection is delivered into the pre-cannulated jugular vein of young (190-220 g) male Sprague Dawley rats (see below for procedure). At the same time osmotic mini pumps are implanted subcutaneously (see below for procedure) to deliver drugs at a constant rate over the course of the study. Depending on the length of the study, a second mini pump may need to be implanted.

In order to confirm the diabetic state, animals have a blood sample taken from the tail (snip the end off the tail) and their blood glucose determined. Animals with blood glucose levels exceeding 13 mM are considered diabetic and randomized into 4 groups. Two groups receive insulin injections subcutaneously daily to achieve partial glucose control (fasting glucose levels approximately 50% of uncontrolled diabetic animals). One of the partially controlled diabetic groups is treated with the test compound. In addition, two non-diabetic groups are included, one receives the test compound and one does not. Neither of the non-diabetic groups of rats receive insulin.

On a weekly basis, 500 μL blood samples are taken by retro-orbital eye bleed, in isofluorane-anesthetized animals for determinations of the following: blood glucose, serum non-esterified free fatty acids, serum triglycerides, HbA1c, serum insulin, total cholesterol, HDL cholesterol, and serum concentrations of the test compound. Body weight is also measured weekly.

Once stable HbA1c is reached, the study is terminated. When this is established, animals are cannulated in the carotid artery following aseptic techniques. Blood pressure is measured in anesthetized and awake rats. The next day, an oral glucose tolerance test is performed. An oral glucose tolerance test involves administering 1 g glucose/kg by gavage.

Arterial blood samples (0.3 ml) are collected through the jugular catheter that was previously used for measuring blood pressure, prior to and at 10, 20, 30, and 60 min following the glucose challenge and the plasma separated for glucose and insulin assays.

Induction of STZ-Diabetes and Implantation of Osmotic Mini Pumps.

Under isofluorane anesthesia, the tails of rats are cleaned with warm water followed by ethanol. A tail vein injection of either STZ or saline is made under anesthesia, using sterile needles and syringe and filter-sterilized solutions. Following i.v. injection, the area has pressure applied to prevent bleeding, and the animal is placed in a clean cage with sterile bedding. In addition to the STZ or saline injection, at the initial time of anesthesia, rats have mini-pumps implanted subcutaneously in the neck region. If the study proceeds beyond 4-weeks, a second implantation is performed. Basically, a small area of the neck is shaved and cleaned extensively with an iodine solution, a small 1-cm incision using a scalpel is made in the dermal layer and the pump is inserted aseptically port-first into the Sub-Q space. The incision is then closed with 1-2 surgical staples as required.

Implantation of Carotid Artery Catheter for Measurement of Blood Pressure and Implementation of Oral Glucose Tolerance Test.

Following conditions using sterile techniques and instruments, an anesthetized rat is laid on its back with the head toward the surgeon and lubricating ointment placed in both eyes. A midline incision is made along the neck to expose the left common carotid artery. A tunnel is made for the catheter using blunt dissection in the subcutaneous pocket on the dorsal section of the neck where it is externalized. Half-curved forceps are used to isolate the artery and soft plastic tubing passed under the posterior portion of the artery to temporarily impede the blood flow to the isolated area. The anterior portion of the external carotid artery is then ligated with a piece of 4-0 silk suture and light tension is created on the artery by anchoring a pair of hemostats to the ends of the suture material. The external carotid is then semi-transected and a 0.033 or 0.040 mm O.D. catheter inserted and pushed toward the aorta, (around 2-3-cm deep). The catheter is tied in place, secured to the pectoral muscle to prevent removal of the catheter, and the anterior portion of the external carotid permanently ligated and observed for any leakage of blood. Externally, the catheter is tied at the back of the neck and a piece of suture tied around the knot leaving both ends about 2 inches long for retrieval from under the skin. The knotted catheter is retracted back under the skin to prevent being pulled out by the rat. For blood pressure measurements, the catheter is attached to a pressure transducer and a data-acquisition system. For blood glucose tolerance testing, the catheter is attached to a needle and syringe for collection of blood samples.

EXAMPLE 8

In order to study the anti-diabetic actions of the compounds, insulin-dependent diabetes mellitus are induced by chemical destruction of the pancreas with an i.v. injection of STZ (60 mg/kg, controls are given saline vehicle). The volume of the injection is equivalent to 0.1 ml/100 g body weight. The injection is delivered into the pre-cannulated jugular vein of young (280-300 g) male Sprague Dawley rats with 2 catheters surgically implanted in the jugular vein and external carotid artery. In order to confirm the diabetic state, animals have a blood sample taken from the cannula and their blood glucose is determined. Animals with blood glucose levels exceeding 13 mM are considered diabetic. The pre-implanted catheter is flushed daily with heparinized saline to maintain patency. One week after the induction of diabetes, rats undergo pharmacokinetic studies with the compounds of the invention. Animals have their catheters retrieved from under the skin and tested for patency. An injection plug is attached to a 19-gauge IV set, filled with 0.1% heparinized saline and the needle end inserted into the catheters. The test compound(s) is (are) administered via the jugular vein catheter either by bolus injection or steady infusion, or by oral gavage (1 ml/kg and 2 ml/kg, respectively). At 10 time points using 5-6 animals, 300 μl of blood is drawn from the line in the carotid artery and 300 μl saline flushed in to replace blood volume. 300 μl of blood at 10 time points from a 300 μm animal represents 10% total blood volume. If a 24-hour sample is drawn, the catheters are tied off at skin level and the animals returned to their cages. They are then sacrificed at 24 hours by exanguination under anesthesia to collect the last blood sample. If there is no 24-hour sample, the animals are sacrificed by exanguination under anesthesia at the last blood collection.

EXAMPLE 9

Exercise Performance and Hemoglobin A1c in Angina Patients with Diabetes

The CARISA (Combination Assessment of Ranolazine in Stable Angina) study randomized 823 symptomatic chronic angina patients on diltiazem, atenolol or amlodipine to ranolazine 750 mg bid, 1000 mg bid or placebo in a parallel, double-blind, 12 week study. Modified Bruce treadmill tests were performed at baseline, and after 2, 6, and 12 weeks of treatment at trough and peak plasma levels. The ranolazine formulation used in this study was that shown in Example 4.

Figure 3:
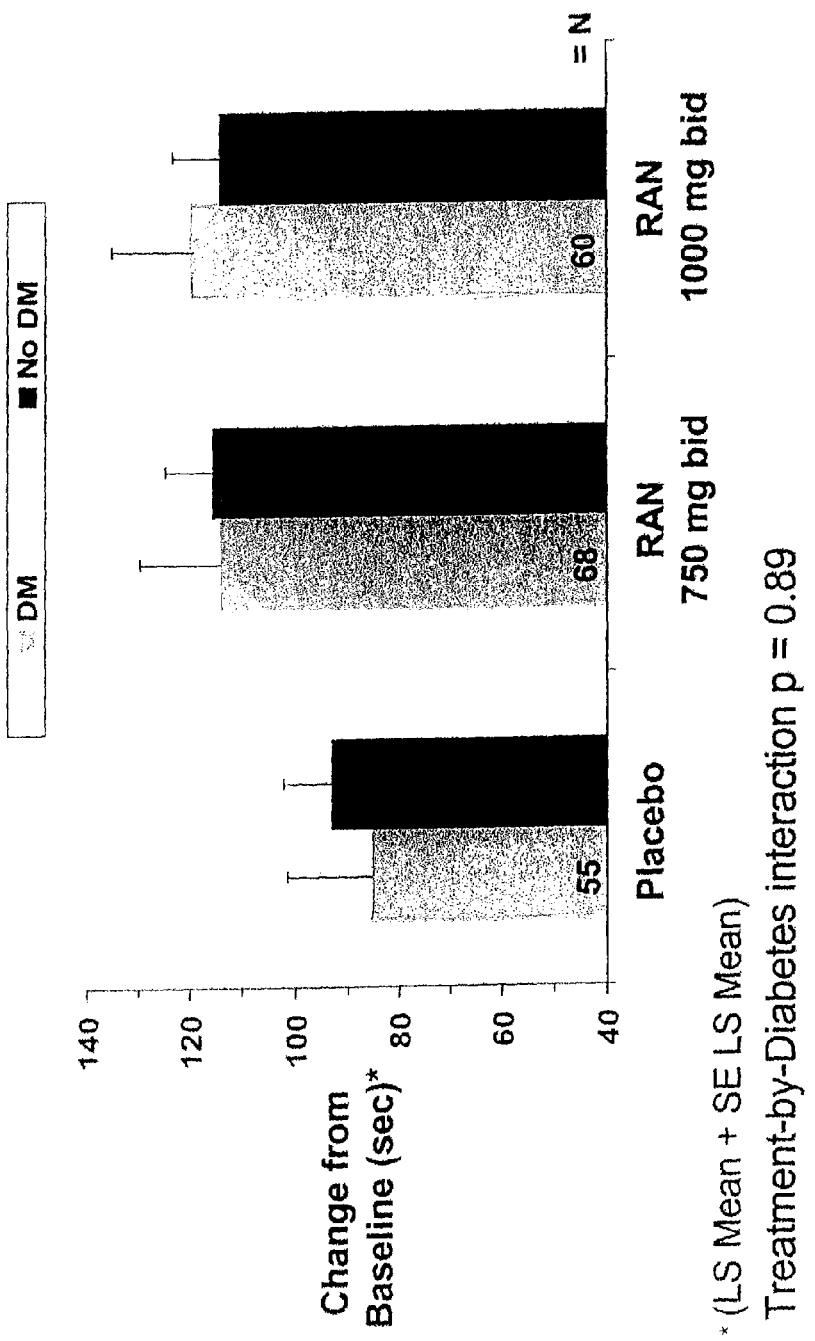
FIG. 3. CARISA Primary Endpoint: Exercise Duration at Trough. This figure shows changes from baseline (in sec) for diabetics and non-diabetics on placebo, 750 mg ranolazine bid, or 1000 mg ranolazine bid.
Figure 4:
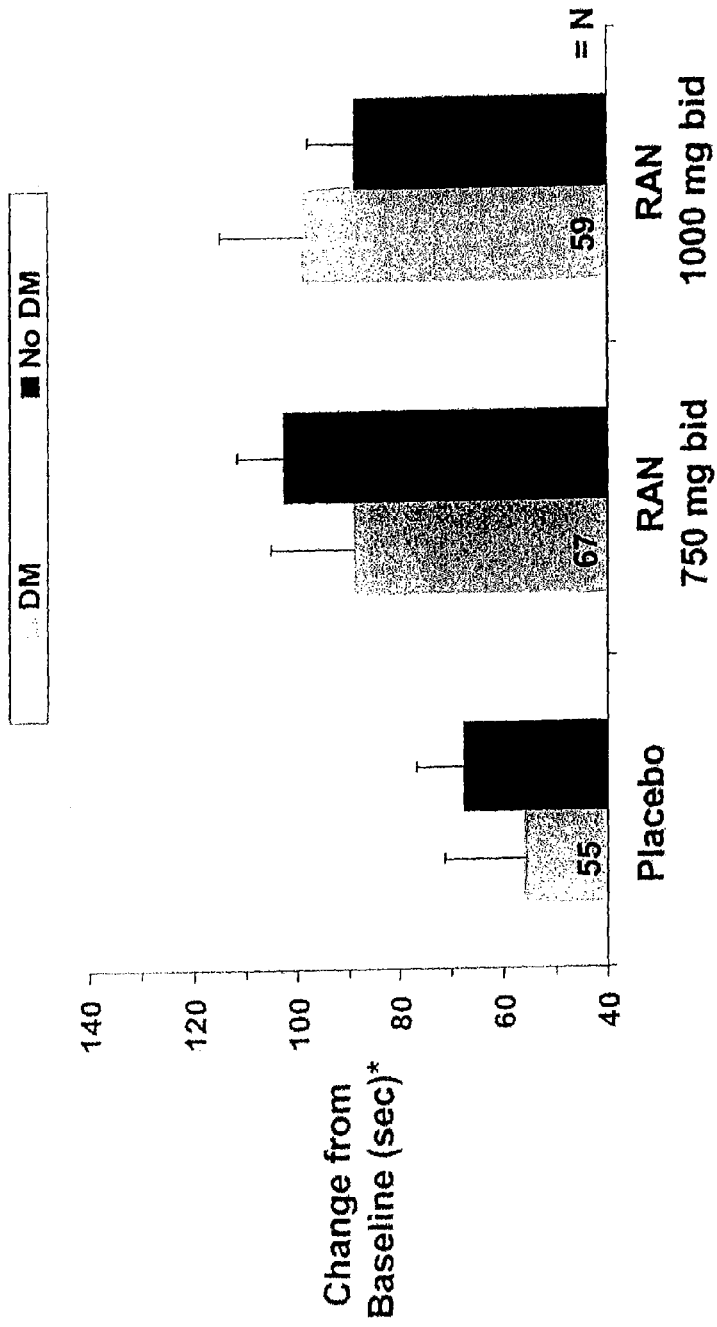
FIG. 4. CARISA: Exercise Duration at Peak. This figure shows changes from baseline (in sec) for diabetics and non-diabetics on placebo, 750 mg ranolazine bid, or 1000 mg ranolazine bid.

Ranolazine prolonged exercise duration (ED) similarly in both diabetic (D) and non-diabetic (ND) patients at trough (FIG. 3) and peak (FIG. 4). The 750 mg dose of ranolazine prolonged exercise duration at trough drug concentrations by 29 seconds in angina patients with diabetes and by 22 seconds in non-diabetic angina patients. The 1000 mg dose of ranolazine prolonged exercise duration at trough drug concentrations by 34 seconds in angina patients with diabetes and by 21 seconds in non-diabetic angina patients.

Figure 5:
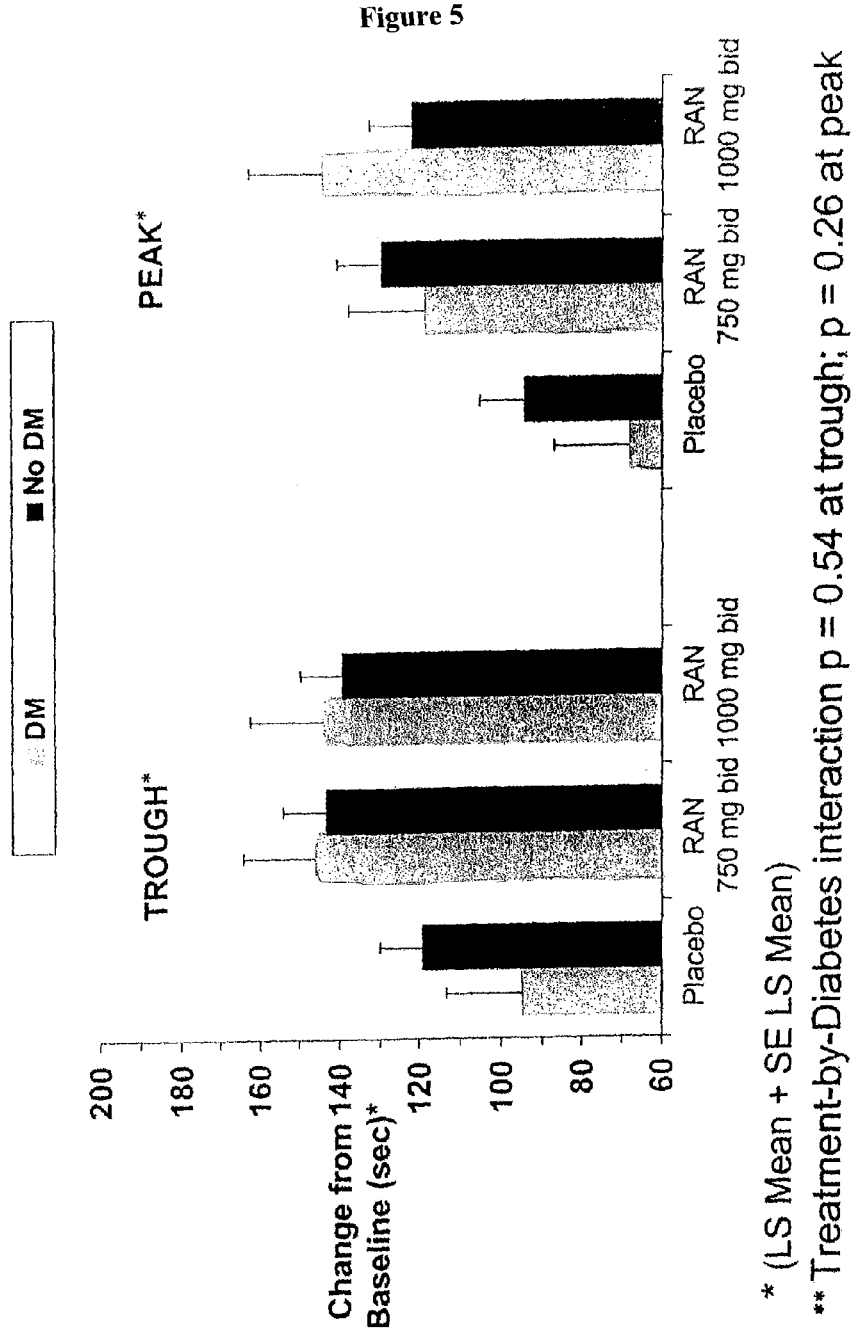
FIG. 5. CARISA: Exercise Time to Onset of Angina. This figure shows changes from baseline (in sec) in trough and peak for diabetics and non-diabetics on placebo, 750 mg ranolazine bid, or 1000 mg ranolazine bid.

Time to angina increased on ranolazine (FIG. 5) and angina frequency decreased. The improvement with ranolazine was not significantly different in D vs. ND patients (treatment by diabetes interaction p-values ≥0.26). Adverse events were similar: 25%, 25% and 34% of D had at least one adverse event on placebo, ranolazine 750 and 1000 mg respectively vs. 27%, 33%, and 32% in ND patients.

Figure 6:
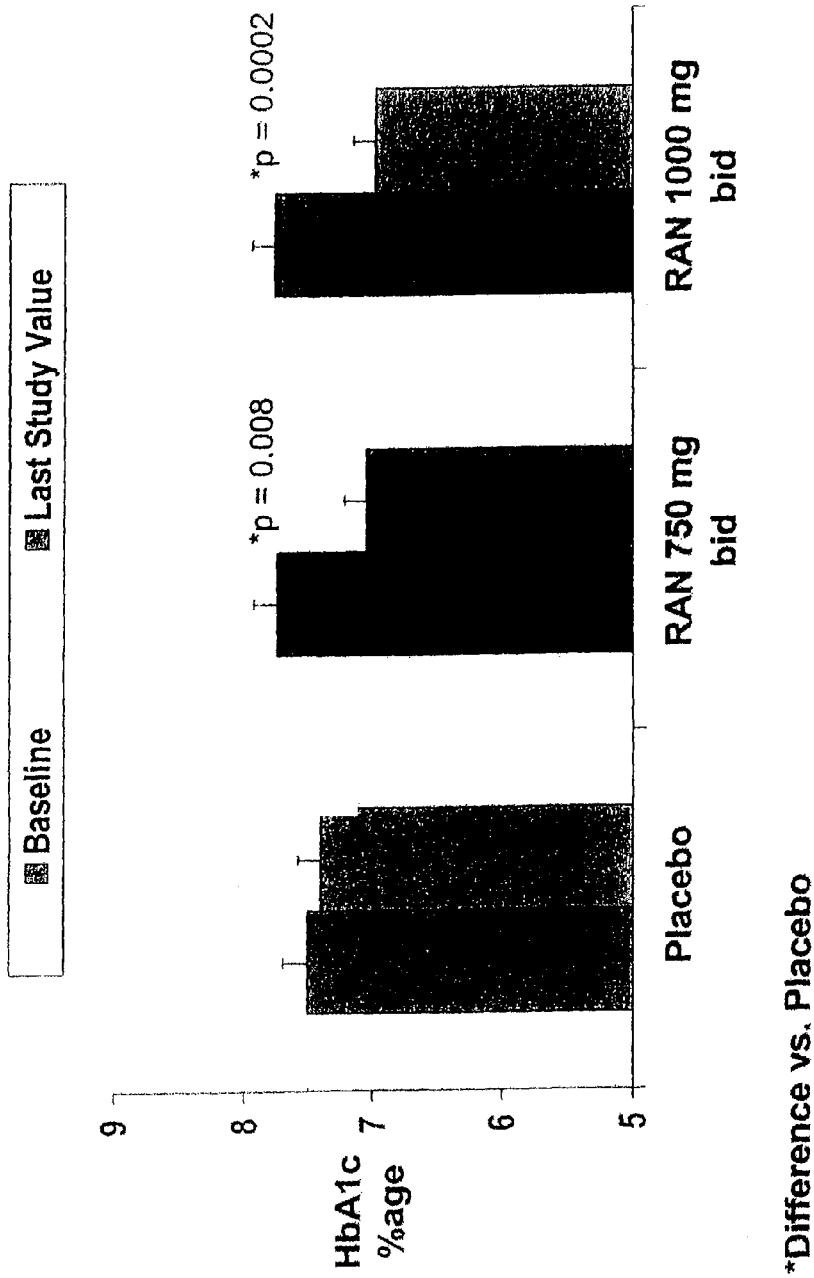
FIG. 6. CARISA: Change from Baseline in HbA1c (all diabetic patients). This figure shows percentage of HbA1c for diabetics on placebo, 750 mg ranolazine bid, or 1000 mg ranolazine bid at baseline and at last study value.
Figure 7:
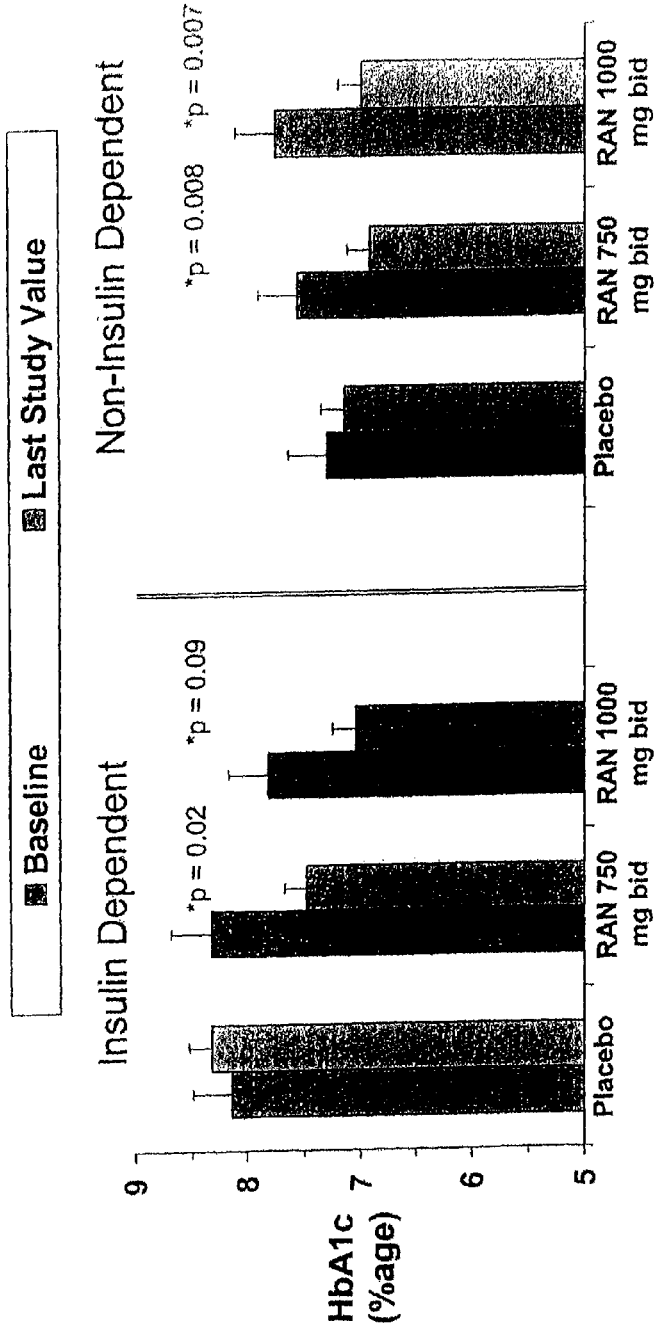
FIG. 7. CARISA: Change from Baseline in HbA1c (Dependent vs Non-insulin Dependent Diabetic Patients. This figure shows percentage of HbA1c for both insulin dependent and non-insulin dependent diabetics on placebo, 750 mg ranolazine bid, or 1000 mg ranolazine bid at baseline and at last study value.

Ranolazine 750 and 1000 mg bid were associated with an average absolute reduction HbA1c of 0.48 percentage points and 0.70 percentage points, respectively compared to placebo at 12 weeks (p<0.01) (FIG. 6). The reductions were greater in those patients on insulin (0.8 and 1.1 percentage points, respectively) (FIG. 7). Glucose and triglyceride values for the diabetic patients in the study are shown in Table 2.

TABLE 2

Glucose and Triglyceride Values (all diabetic patients)

| | Placebo | RAN 750 mg bid | RAN 1000 mg bid |
|---|---|---|---|
| Glucose (mg/dL) | | | |
| Baseline | 177.8 ± 10.8 | 168 ± 8.0 | 165.2 ± 7.8 |
| Change from baseline | 1.2 ± 7.1 | 8.0 ± 8.8 | 1.7 ± 7.2 |
| Triglycerides (mg/dL) | | | |
| Baseline | 233.0 ± 56.8 | 192.0 ± 14.5 | 196 ± 17.5 |
| Change from Baseline | 26.3 ± 21.2 | 21.2 ± 13.5 | −7.3 ± 9.3 |

All values are Mean ± SEM

EXAMPLE 10

Carbohydrate and Lipid Parameters in MARISA and CARISA

Ranolazine (RAN) increased treadmill exercise capacity in patients with chronic angina both alone (MARISA, N=191) and when added to background anti-anginal therapy with atenolol, diltiazem, or amlodipine (CARISA, N=823). Angina frequency and nitroglycerin consumption were reduced by ranolazine. The ranolazine formulation used in the CARISA and MARISA studies was that shown in Example 4. The most frequently reported adverse events (dizziness constipation and nausea) were generally mild and occurred in fewer than 10% of patients. The potential use of ranolazine in diabetics is of interest because approximately one in four angina patients has diabetes.

Efficacy and tolerability of ranolazine were similar in both diabetic and non-diabetic patients in both MARISA and CARISA. In diabetic patients in CARISA (N=131), ranolazine 750 and 1000 mg bid were associated with a mean absolute reduction in HbA1c of 0.48 percentage points and 0.70 percentage points, respectively, compared to placebo at 12 weeks (each p<0.01). The reductions versus placebo were greater in those patients on insulin (N=31; 0.84 and 1.05 percentage points), on 750 and 1000 mg bid (p<0.02 and p<0.01), respectively. Fasting glucose was not affected by ranolazine in diabetic patients in CARISA, regardless of insulin treatment; one hypoglycemic episode was reported on placebo and one on ranolazine. After 12-24 months of open-label treatment, HbA1c decreased from baseline in the diabetic patients by 1.1 percentage points. During the first 12 weeks of ranolazine treatment of diabetic patients in CAR-ISA, mean total and LDL cholesterol increased by up to 16 and 11 mg/dL, respectively; however, because of mean increases in HDL cholesterol up to 5 mg/dL, the HDL/LDL ratio changed little. Over 3 years of open-label treatment in the combined MARISA/CARISA diabetic population, total and LDL cholesterol decreased from baseline, while HDL cholesterol continued to increase.

EXAMPLE 11

Effect of Ranolazine on Hyperglycemia in the MERLIN-TIMI 36 Randomized Controlled Trial Background A prospective evaluation of the effect of ranolazine on hyperglycemia as part of a randomized, double-blind, placebo-controlled trial in acute coronary syndromes (ACS).

Methods

MERLIN-TIMI 36 randomized patients with non-ST elevation ACS to ranolazine or placebo to compare HbA1c (%) and the time to onset of worsening hyperglycemia (>1% increase in HbA1c). HbA1c data are reported as least-square means. Patients categorized as "diabetic" had been diagnosed as diabetic before or at the time of randomization. Patients categorized as "no diabetes" had not been diagnosed as diabetic before or at the time of randomization. Some patients characterized as "no diabetes" may have been diagnosed as "diabetic" during the trial; however, these patients are still listed in the "no diabetes" category in FIG. 8B.

Results

Among 4306 patients with serial measurements, ranolazine significantly reduced HbA1c at 4 months compared with placebo (5.9% vs. 6.2%, change from baseline −0.30 vs. −0.04 p=0.001). In patients with DM treated with ranolazine, HbA1c declined from 7.2 to 6.8 (Δ−0.64, p<0.001, see FIG. 8A). As such, patients with DM were significantly more likely to achieve an HbA1c <7% at 4 months when treated with ranolazine versus placebo (59% vs. 49%, p<0.001). In addition, worsening of hyperglycemia by 1 year of follow-up was less likely in diabetic patients treated with ranolazine (14.2% vs. 20.6%; HR 0.63; 95% CI 0.51, 0.77, p<0.001). Notably, in patients without DM at randomization or baseline (fasting glucose <100 mg/dL and HbA1c <6%), the incidence of new fasting glucose >110 mg/dL or HbA1c ≥6% was also reduced by ranolazine (31.8% vs. 41.2%; HR 0.68; 95% CI 0.53, 0.88; p=0.003; see FIG. 8B). Reported hypoglycemia in patents with DM was similar between treatment groups (3% vs 3$).

Conclusion

Ranolazine significantly improved HbA1c in patients with DM and reduced the incidence of newly increased HbA1c in those without evidence of previous hyperglycemia.

What is claimed is:

1. A method for treating diabetes in a human patient in need thereof, comprising administering to the patient a therapeutically effective amount of ranolazine, as a racemic mixture or a pharmaceutically acceptable salt thereof, wherein the patient suffers from a cardiovascular disease and metabolic syndrome.

2. The method of claim 1, wherein the ranolazine is administered to the patient orally.

3. The method of claim 2, wherein the ranolazine is administered as an immediate release formulation.

4. The method of claim 2, wherein the ranolazine is administered as a sustained release formulation.

5. The method of claim 2, wherein the ranolazine is administered in a formulation that has both immediate release and sustained release aspects.

6. The method of claim 4, wherein the sustained release formulation provides a plasma level of ranolazine between 550 and 7500 ng base/ml over a 24 hour period.

7. The method of claim 4, wherein the sustained release formulation comprises at least 50% by weight ranolazine, a pH dependent binder, and a pH independent binder.

8. The method of claim 7, wherein the sustained release formulation comprises at least 50% by weight ranolazine, from about 5 to about 12.5% by weight methacrylic acid copolymer, from about 1 to about 3% by weight of hydroxypropyl methylcellulose, microcrystalline cellulose, sodium hydroxide, and magnesium stearate.

9. The method of claim 1, wherein the cardiovascular disease is selected from the group consisting of heart failure, congestive heart failure, acute heart failure, ischemia, recurrent ischemia, myocardial infarction, arrhythmias, acute coronary syndrome, and intermittent claudication.

10. The method of claim 1, wherein the patient is a Type II diabetic patient.

* * * * *

UNITED STATES PATENT AND TRADEMARK OFFICE
CERTIFICATE OF CORRECTION

PATENT NO.      : 8,822,473 B2
APPLICATION NO. : 11/756499
DATED           : September 2, 2014
INVENTOR(S)     : Andrew Wolff et al.

It is certified that error appears in the above-identified patent and that said Letters Patent is hereby corrected as shown below:

TITLE PAGE

Item (56) References Cited, add --GRYNBERG, Modifications due Metabolisme Energetique Cardiaque Chez le Diabetique, Diabetes and Metabolims, vol. 27, no. 5, November 2001, pages 4S12-4S19, page 4S16, column 2, line 5, page 4S17, column 1, line 36--.

IN THE SPECIFICATION

Column 32, Line 46, replace "(3% vs 3$)" with --(3% vs 3%)"--.

Signed and Sealed this
Third Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,822,473 B2 | Page 1 of 1 |
| APPLICATION NO. | : 11/756499 | |
| DATED | : September 2, 2014 | |
| INVENTOR(S) | : Andrew Wolff et al. | |

It is certified that error appears in the above-identified patent and that said Letters Patent is hereby corrected as shown below:

IN THE SPECIFICATION

In Column 10, Line 34, please replace "where R. is lower alkyl" with --where R is lower alkyl--.

Signed and Sealed this

Thirteenth Day of October, 2015

Michelle K. Lee
*Director of the United States Patent and Trademark Office*